United States Patent
Kadota et al.

(10) Patent No.: US 7,595,414 B2
(45) Date of Patent: Sep. 29, 2009

(54) METAL COMPLEX COMPOUND COMPRISING β-DIKETONATO LIGAND

(75) Inventors: Takumi Kadota, Yamaguchi (JP);
Chihiro Hasegawa, Yamaguchi (JP);
Kouhei Watanuki, Yamaguchi (JP);
Hiroyuki Sakurai, Yamaguchi (JP);
Hiroki Kanato, Yamaguchi (JP)

(73) Assignee: UBE Industries, Ltd., Ube-Shi, Yamaguchi (JP)

( * ) Notice: Subject to any disclaimer, the term of this patent is extended or adjusted under 35 U.S.C. 154(b) by 489 days.

(21) Appl. No.: 10/592,876

(22) PCT Filed: Mar. 15, 2005

(86) PCT No.: PCT/JP2005/004577

§ 371 (c)(1),
(2), (4) Date: Sep. 14, 2006

(87) PCT Pub. No.: WO2005/087697

PCT Pub. Date: Sep. 22, 2005

(65) Prior Publication Data

US 2008/0254216 A1 Oct. 16, 2008

(30) Foreign Application Priority Data

| Mar. 15, 2004 | (JP) | 2004-072471 |
| Mar. 30, 2004 | (JP) | 2004-097670 |
| Apr. 6, 2004 | (JP) | 2004-111705 |
| Jun. 17, 2004 | (JP) | 2004-180106 |
| Oct. 12, 2004 | (JP) | 2004-297245 |
| Nov. 12, 2004 | (JP) | 2004-328357 |
| Jan. 19, 2005 | (JP) | 2005-011264 |
| Feb. 7, 2005 | (JP) | 2005-030220 |

(51) Int. Cl.
*C07C 49/92* (2006.01)
*C07F 5/00* (2006.01)
*C23C 16/00* (2006.01)

(52) U.S. Cl. ......... 556/40; 534/15; 568/415; 427/248.1

(58) Field of Classification Search .......... 556/40; 534/15; 568/415; 427/248.1
See application file for complete search history.

(56) References Cited

U.S. PATENT DOCUMENTS

| 3,853,918 A | 12/1974 | Van Den Ouweland |
| 6,429,325 B1 | 8/2002 | Onozawa et al. |
| 6,752,869 B2 | 6/2004 | Lee et al. |

FOREIGN PATENT DOCUMENTS

WO    WO 01/48130 A1    7/2001

OTHER PUBLICATIONS

International Preliminary Report on Patentability and Written Opinion of the International Search Authority (PCT/JP2005/004577) mailed Sep. 28, 2006.
International Search Report (PCT/JP2005/004577) mailed Jul. 5, 2005.

*Primary Examiner*—Porfirio Nazario Gonzalez
(74) *Attorney, Agent, or Firm*—Nixon Peabody LLP; Jeffrey L. Costellia

(57) ABSTRACT

To provide a metal complex compound capable of being suitably used for manufacturing a metal-containing thin film by the CVD method and a method for preparing a metal-containing thin film.

A metal complex compound comprising a β-diketonato ligand having an alkoxyalkyl-methyl group, and a method for preparing a metal-containing thin film using the metal complex compound by the CVD method.

11 Claims, 1 Drawing Sheet

METAL COMPLEX COMPOUND COMPRISING β-DIKETONATO LIGAND

FIELD OF THE INVENTION

The present invention relates to a metal complex compound having a β-diketonato ligand which is favorably employable for preparing a metal oxide film or a metal film by chemical vapor deposition method (CVD method).

BACKGROUND OF THE INVENTION

Recently, a number of studies and developments have been performed on metal complex compounds for preparing materials employed in the fields of semi-conductors, electronic elements and optical elements. For instance, complex compounds of metals described in Periodic Table IIA (e.g., strontium, barium and magnesium) are employed and studied as materials for manufacturing ferro-dielectrics and super-conductive elements or materials for preparing a protective film of a plasma display device. Complex compounds of metals described in Periodic Table IIB (e.g., zinc) are employed and studied as materials for manufacturing light-transmitting electro-conductive films and light-emitting elements. Complex compounds of metals described in Periodic Table IIIB (e.g., indium, aluminum, and gallium) are employed and studied as materials for manufacturing light-transmitting electro-conductive films and insulating films of semi-conductor memory gate.

Complex compounds of metals described in Periodic Table IVB (e.g., tin and lead) are employed for manufacturing light-transmitting electro-conductive film and ferro-dielectrics. Complex compounds of metals described in Periodic Table VA (e.g., vanadium) are studied for the purpose of preparing ferro-dielectrics and barrier films for copper wiring of silicon semi-conductors.

Complex compounds of metals described in Periodic Table IVA (e.g., titanium, zirconium and hafnium) are employed for preparing ferro-dielectrics (PZT) and barrier films for copper wiring of silicon semi-conductors. Complex compounds of metals described in Periodic Table VIA (e.g., chromium) are employed for preparing glass for an optical fiber laser and coating of steel surface. Complex compounds of metals described in Periodic Table VIIA (e.g., manganese) are employed and studied as materials for preparing electro-chromism devices and further employed and studied as materials for preparing thermistors due to their wide variation of resistance with temperature and wide temperature resolution. Complex compounds of metals described in Periodic Table VIII (e.g., nickel and cobalt) are studied for preparing films used on silicon semi-conductors for increasing density of copper nuclei generation in copper wiring and increasing adhesion of copper wiring to an under-lying layer.

Complex compounds of metals described in Periodic Table IB (e.g., copper, silver, and gold) are used for manufacturing electro-conductive wiring for the reason that these metals show low electric resistance. Particularly, a number of studies have been conducted on a copper film, because a copper film is employable for manufacturing wiring of silicon semi-conductors. A metal oxide film comprising copper oxide is paid attention as material of a high-temperature super-conductive elements.

Rare earth metals (e.g., scandium, yttrium, and lanthanoids) are paid attention as materials for preparing high-temperature super-conductive element, high dielectrics for a gate insulating film and ferro-dielectrics for PLZT film. Accordingly, the complex compounds of rare earth metals are of value for preparing these materials.

The metal films and metal oxide films are conventionally prepared by the CVD method, because the CVD method can easily give a thin film with uniform thickness Therefore, materials favorably employable in the CVD method are required.

At the present time, metal complex compounds having a β-diketonato ligand are widely employed as materials for preparing a metal atom-containing film by the CVD method. The metal complex compounds having a β-diketonato ligand are good in their stability and sublimation property, and hence are of value as the metal sources for the CVD method. Representative example of the β-diketonato ligands are acetylacetonato (acac) and 2,2,6,6-tetra-methyl-3,5-heptanedionato (dpm).

It is noted that most of known metal complex compounds having a β-diketonato ligand are solid at an ordinary temperature and have a high melting temperature. Therefore, the use of the known metal complex compounds as the metal source in the CVD method is liable to cause plugging in the pipe systems for supplying a metal source, and is not satisfactorily accepted in industry.

For the reason mentioned above, a number of studies have been made for obtaining metal complex compounds having good stability and a low melting temperature. One of the known improvements resides in the attachment of an ether bonding-containing substituent group to the β-diketonato ligand to obtain a metal complex compound having a satisfactory stability and a low melting temperature.

For instance, Patent publication 1 and Non-patent publication 1 (mentioned afterward) describe complex compounds of strontium (described in Periodic Table IIA) having the following formulas (a) and (b):

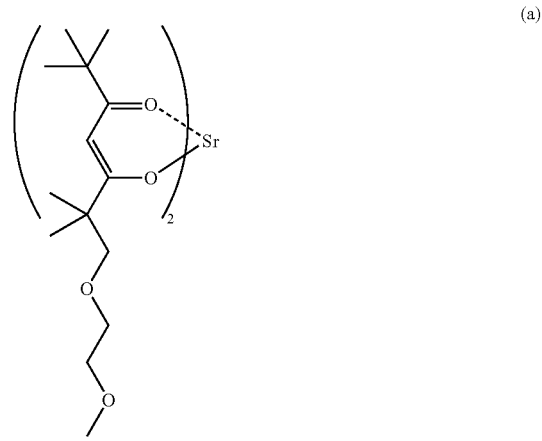

(a)

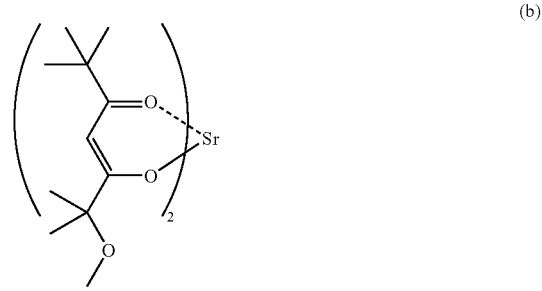

(b)

It is noted that the strontium complex compound of the formula (a) shows improved stability but unfortunately shows a low vapor pressure, and that the strontium complex compound of the formula (b) shows good stability and good sublimation, but unfortunately has a high melting point (235° C.). Therefore, it appears that these complex materials are not favorably employed for the preparation of a strontium film by the CVD method.

Non-patent publication 2 (mentioned afterward) describes a complex compound of zinc (described in Periodic Table IIB) having the following formula:

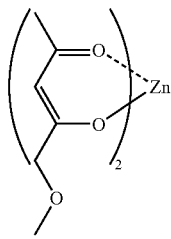

It is noted that the above-mentioned zinc complex compound shows a low thermal stability and easily suffers thermal deterioration. Therefore, it is not easy to supply the zinc complex compound with no troubles.

Patent Publication 2 (mentioned afterward) describes a complex compound of aluminum (described in Periodic Table IIIB) having an ether group-containing ligand which is illustrated below:

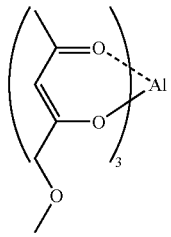

It is noted that the above-mentioned aluminum complex compound shows low thermal stability and hence easily suffers thermal deterioration. Therefore, it is not easy to supply the aluminum complex compound with no troubles.

There are known no studies in connection with gallium complex compounds and indium complex compounds.

Patent Publication 3 (mentioned afterward) describes $Sn(dpm)_2$ as a complex compound of tin (described in Periodic Table IVB). It is noted that the tin complex compound is very sensitive to water. Therefore, it is not easy to handle this tin complex compound.

As for the lead complex compounds, Patent Publications 4 and 5 (mentioned afterward) describe $Pb(dmp)_2$ and bis(1,3-diphenyl-1,3-propanedionato)lead(II). It is noted that these complex con-pounds have a high melting point. Therefore, these complex compounds are not satisfactorily employable for the preparation of a lead film by the CVD method.

As for the complex compound of vanadium (described in Periodic Table VA), Patent Publication 6 (mentioned afterward) describes $V(dpm)_2$. It is noted that this complex compound also has a high melting point. Therefore, this complex compound is not satisfactorily employable for the preparation of a vanadium film by the CVD method.

As for the complex compound of nickel (described in Periodic Table VIII), Non-patent Publication 2 and Patent Publication 7 (mentioned afterward) describe a metal complex compounds having the following formulas (c) and (d):

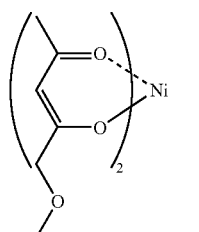

(c)

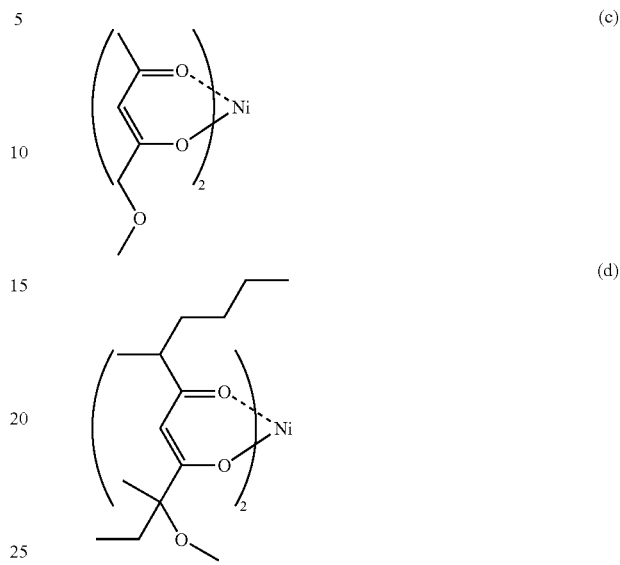

(d)

It is noted that the nickel complex compound of the formula (c) shows poor thermal stability and easily suffers thermal deterioration, and that the nickel complex compound of the formula (d) shows a low vapor pressure due to its high molecular weight.

As for the cobalt complex compound, Patent Publication 8 (mentioned afterward) describes a metal complex compound having the following formula:

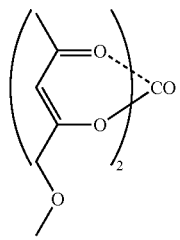

It is noted that the above-mentioned cobalt complex compound shows poor thermal stability and easily suffers thermal deterioration. Therefore, it is not easy to supply the cobalt complex compound with no troubles.

As for the copper complex compound, Patent Publication 9 (mentioned afterward) describes a copper complex compound having the following formula:

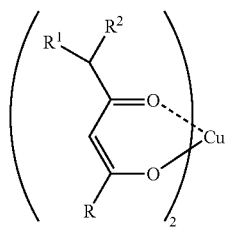

in which R is isopropyl or tert-butyl, $R^1$ is methyl or ethyl, and $R^2$ is propyl or butyl It is noted that the above-mentioned copper complex compound shows no improvement in its rate of copper film formation. Therefore, it is not satisfactorily employable due to its low productivity.

As for the complex compounds of rare earth metals, Patent Publications 10 to 12 describe metal complex compounds having the following formula:

$$\left( \begin{array}{c} R^1 \\ \diagup \\ \diagdown \\ R^2 \end{array} \begin{array}{c} O \\ \diagdown \\ \diagup \\ O \end{array} REM \right)_3$$

in which REM stands for a rare earth metal atom, $R^1$ is isobutyl or t-butyl, and $R^2$ is isopropyl, isobutyl, t-butyl, 1-ethylpentyl or 2-(2-methoxyethoxy)-1,1'-dimethylethyl.

It is noted that the above-mentioned rare earth metal complex compounds have a high melting point and is insoluble or sparingly soluble in organic solvents. Further, the film formation needs a high temperature operation.

Patent Publication 1: JP-A-9-136857
Patent Publication 2: DE-A-2207866
Patent Publication 3: JP-A-6-234779
Patent Publication 4: JP-A-2002-155008
Patent Publication 5: JP-A-2003-226664
Patent Publication 6: JP-A-2003-49269
Patent Publication 7: WO 01/48130
Patent Publication 8: JP-A-2-121944
Patent Publication 9: JP-A-2001-181840
Patent Publication 10: JP-A-2003-321475
Patent Publication 11: JP-A-4-72066
Patent Publication 12: JP-A-9-228049
Non-patent Publication 1: Zhurnal Neorgaicheskoi Khimiii, 36(9), 2279 (1991)
Non-patent Publication 2: Inorg. Chem., 1(2), 404 (1962)

DISCLOSURE OF THE INVENTION

Problems to be Solved by the Invention

It is an object of the invention to provide metal complex compounds which has a low melting point, good stability to water, air and heat, and therefore which is favorably employable for the preparation of metal-containing films by the CVD method.

Invention to Solve the Problems

The present invention resides in a metal complex compound having a β-diketonato ligand which has an alkoxyalkylmethyl group.

The β-diketonato ligand of the metal complex compound according to the invention preferably has the following formula (1):

$$\begin{array}{c} X \\ | \\ Z- \\ | \\ Y \end{array} \begin{array}{c} O \\ \diagdown \\ \diagup \\ O \end{array} \quad (1)$$

$$\begin{array}{c} H \quad R^a \\ R^b \diagdown O \diagup \end{array} \quad (2)$$

wherein X stands for an alkoxyalkylmethyl having the above-mentioned formula (2) in which each of $R^a$ and $R^b$ independently represents a linear or branched alkyl group having 1 to 5 carbon atoms; Y stands for an alkoxy-alkylmethyl of the above-mentioned formula (2) or a linear or branched alkyl group having 1 to 8 carbon atoms; and Z stands for a hydrogen atom or an alkyl group having 1 to 4 carbon atoms.

The metal complex compound of the invention preferably is represented by the formula (3):

$$\left( \begin{array}{c} X \\ | \\ Z- \\ | \\ Y \end{array} \begin{array}{c} O \\ \diagdown \\ \diagup \\ O \end{array} M \right)_n \quad (3)$$

in which M stands for a metal atom; each of X, Y, and Z has the same meaning, and n is an integer of 1 to 4.

M preferably is a metal atom described in Periodic Table IIA, IIB, IIIB, IVB or VA. It is particularly preferred that M is an atom of metal selected from the group consisting of magnesium, calcium, strontium, barium, zinc, born, aluminum, gallium, indium, geranium, tin, lead, vanadium, niobium, and tantalum.

Further, M preferably is a metal atom described in Periodic Table IVA, VIA, VIIA, or VIII. It is particularly preferred that M is an atom of metal selected from the group consisting of titanium, zirconium, hafnium, chromium, manganese, nickel, cobalt, iron, ruthenium, and iridium.

Furthermore, M preferably is a metal atom described in Periodic Table IB, and n preferably is 1 or 2. It is particularly preferred that M is a metal atom selected from the group consisting of a copper atom, a silver atom, and a gold atom.

Furthermore, M preferably is a rare earth metal atom, and n preferably is 3 or 4. It is particularly preferred that M is an atom of metal selected from the group consisting of yttrium, lanthanum, cerium, praseodymium, neodymium, samarium, europium, erbium, ytterbium, and lutetium, and n is 3 or 4.

The invention further resides in a process for preparing a metal oxide film which comprises the steps of: heating a metal complex compound having a β-diketonato ligand which has an alkoxyalkylmethyl group to give a vapor of the metal complex compound and supplying the vapor into a reaction chamber in which a substrate is placed; and bringing the vapor into contact with oxygen or steam in the reaction chamber under heating to decompose the vapor to convert into a metal oxide vapor and depositing the metal oxide vapor on a surface of the substrate.

In the above-mentioned process for preparing a metal oxide film, the heating of a metal complex compound in the step is preferably performed by heating a solution which is prepared by dissolving a metal complex compound in an organic solvent (particularly, an aliphatic hydro-carbon solvent, an aromatic hydrocarbon solvent or an ether solvent).

The invention furthermore resides in a process for preparing a metal film which comprises the steps of: heating a metal complex compound having a β-diketonato ligand which has an alkoxyalkylmethyl group to give a vapor of the metal complex compound and supplying the vapor into a reaction chamber in which a substrate is placed; and bringing the vapor into contact with hydrogen in the reaction chamber under heating to decompose the vapor to convert into a metal vapor and depositing the metal vapor on a surface of the substrate.

In the above-mentioned process for preparing a metal film, the heating of a metal complex compound in the step is also preferably performed by heating a solution which is prepared by dissolving a metal complex compound in an organic solvent (particularly, an aliphatic hydrocarbon solvent, an aromatic hydrocarbon solvent or an ether solvent).

EFFECTS OF INVENTION

The use of the metal complex compound of the invention in the process for preparing a metal film or a metal oxide film by the CVD method enables to prepare a metal film or a metal oxide film having good film characteristics with little troubles in its preparation steps in a relatively short period of time.

PREFERRED EMBODIMENTS OF INVENTION

Figure 1:
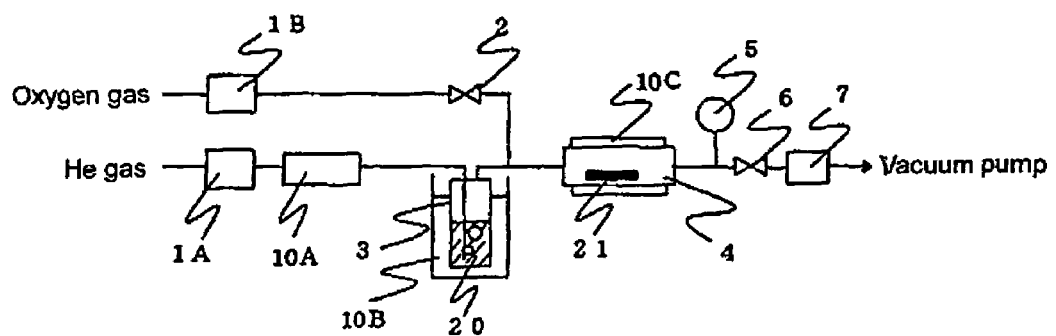
FIG. 1 illustrates a constitution of a deposition apparatus.

The metal complex compound which has a β-diketonato ligand having an alkoxyalkylmethyl group is represented by the aforementioned formula (1), and the metal complex compound of the invention is represented by the aforementioned formula (3).

In the formula (1), X is an alkoxyalkylmethyl group having the formula (2) in which each of $R^a$ and $R^b$ represents a linear or branched alkyl group having 1 to 5 carbon atoms, such as methyl, ethyl, n-propyl, isopropyl, n-butyl, isobutyl, t-butyl, or pentyl; Y is a group of the formula (2) or a linear or branched alkyl group having 1 to 8 carbon atoms, such as methyl, ethyl, n-propyl, isopropyl, n-butyl, isobutyl, t-butyl, pentyl, hexyl, heptyl, or octyl; Z is a hydrogen atom or a linear or branched alkyl group having 1 to 4 carbon atoms, such as methyl, ethyl, n-propyl, isopropyl, n-butyl, isobutyl, or t-butyl; and n is an integer of 1 to 4.

The ligand of the metal complex compound of the invention, that is, the β-diketonato ligand having an alkoxyalkylmethyl group, can be easily prepared in a manner similar to the manner known for the preparation of the known β-diketones. Representative preparing processes are described hereinafter in Reference Examples.

Examples of the metal complex compounds of the invention which has a β-diketonato ligand having an alkoxy-alkylmethyl group are illustrated below:

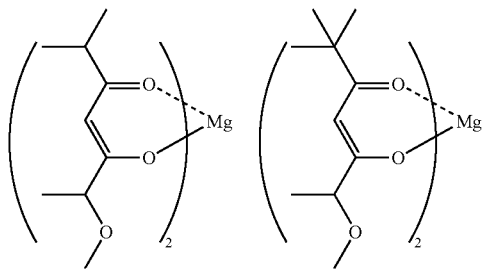

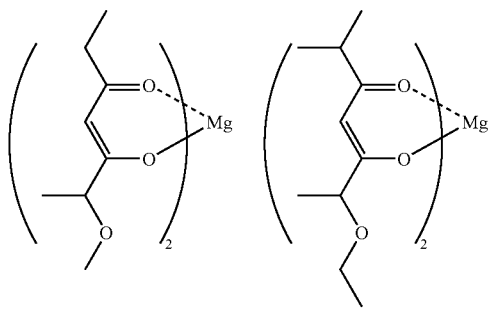

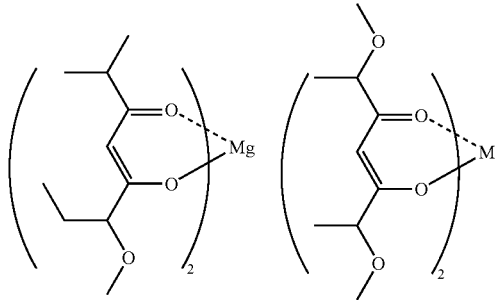

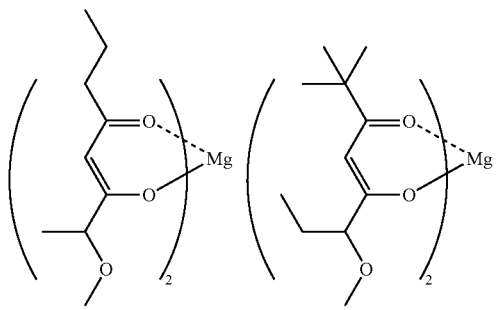

-continued
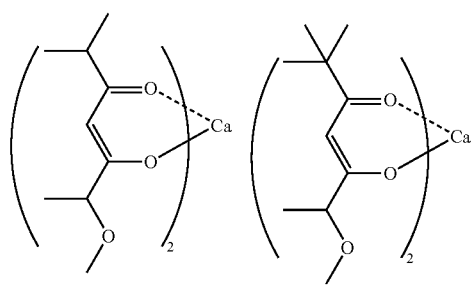
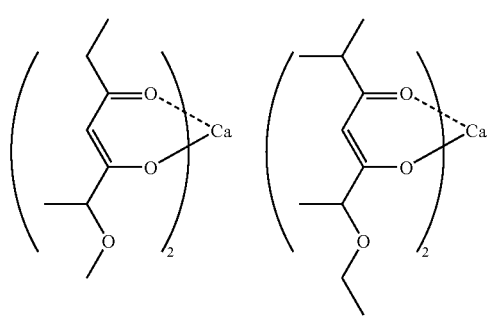
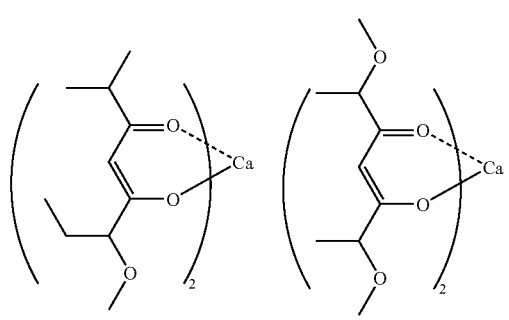
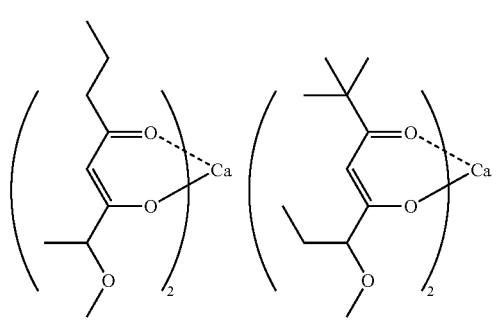
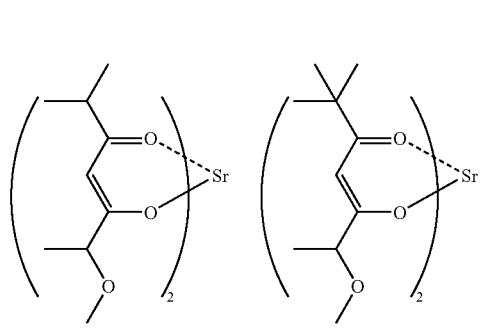
-continued
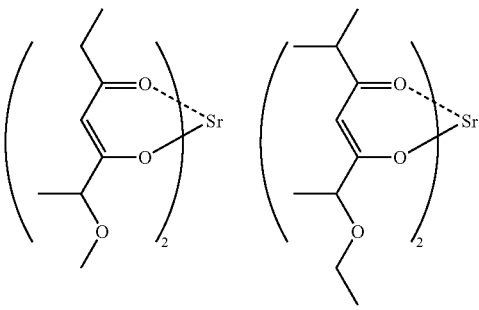
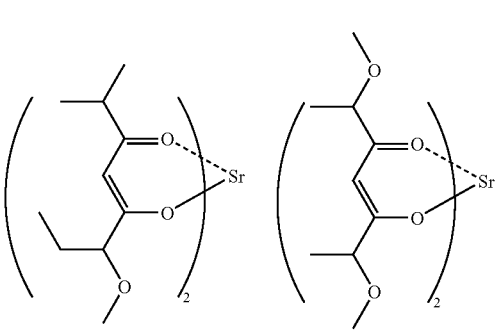
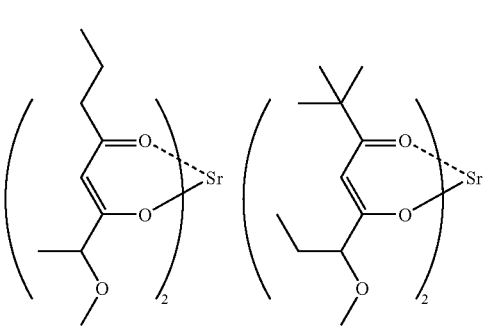
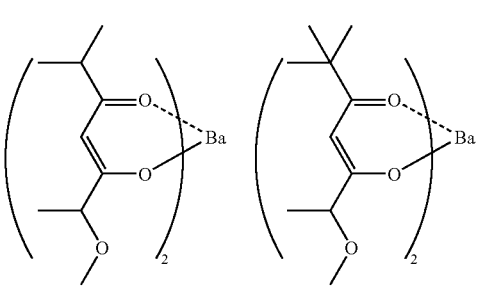
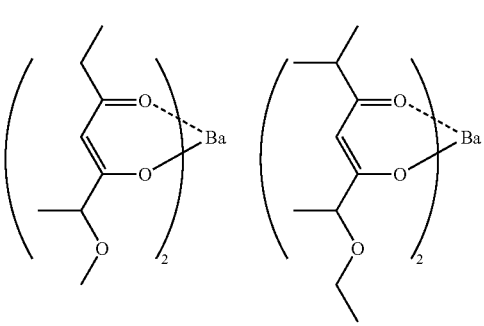

-continued

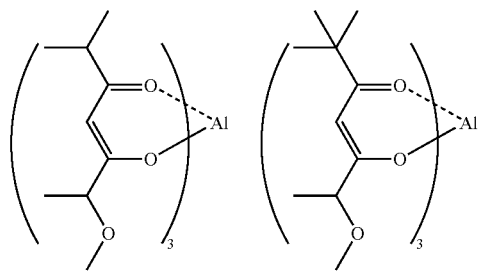
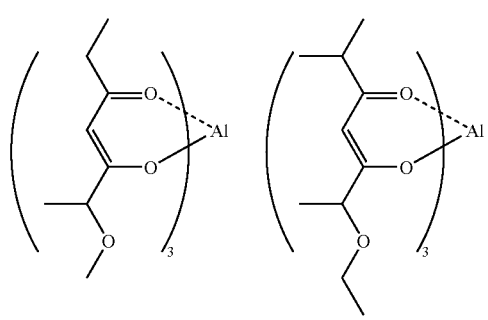
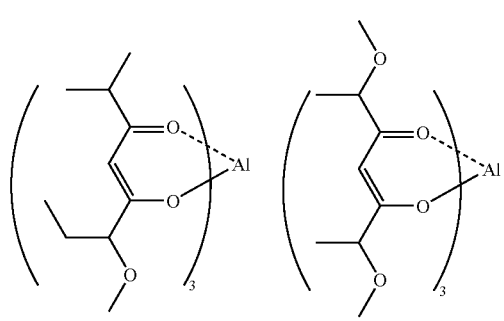
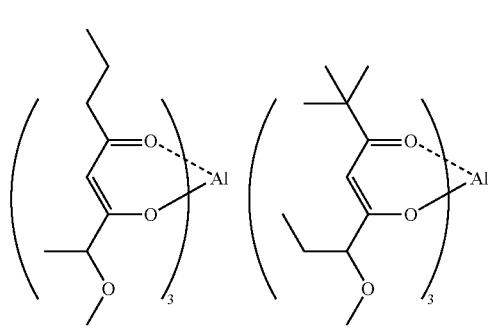
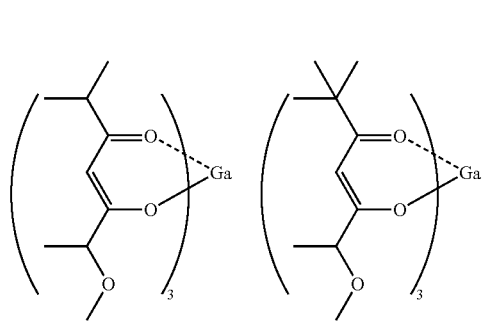
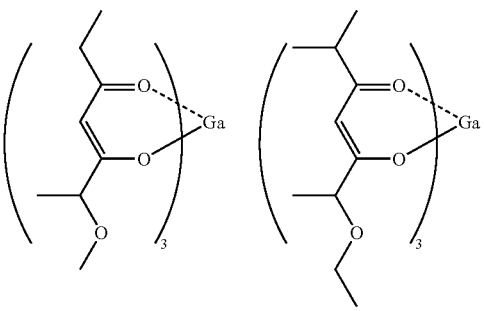
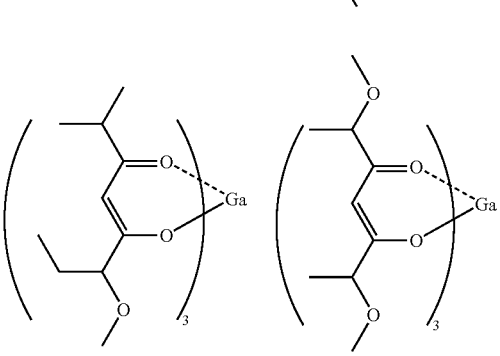
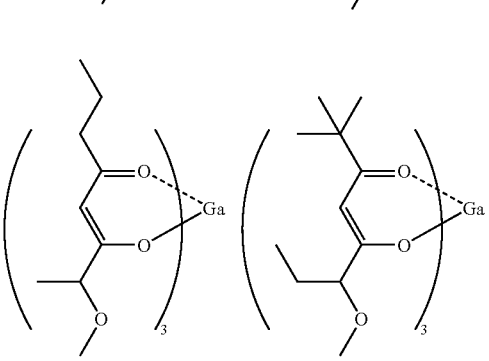
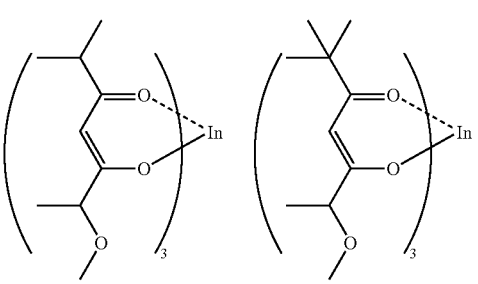
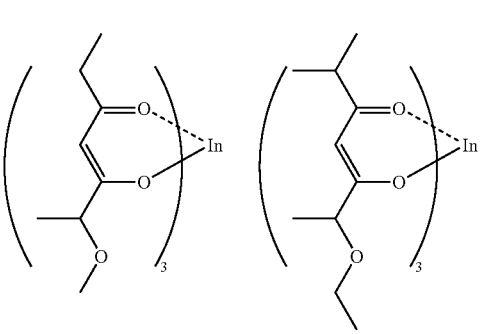

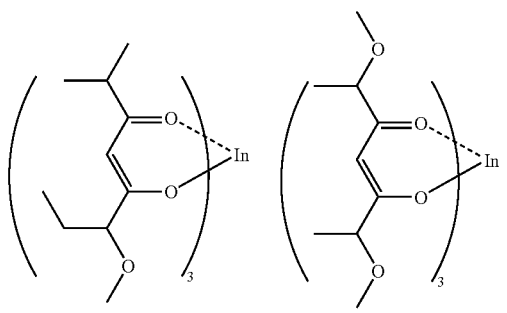
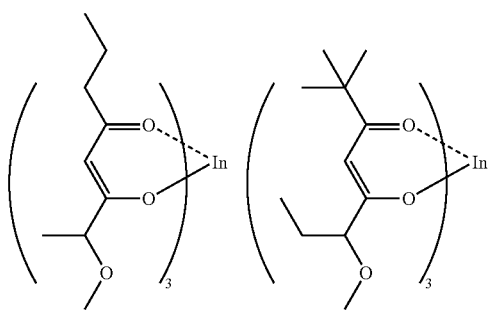
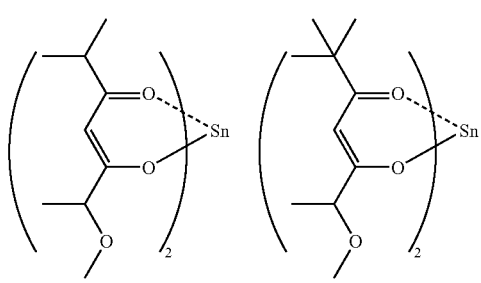
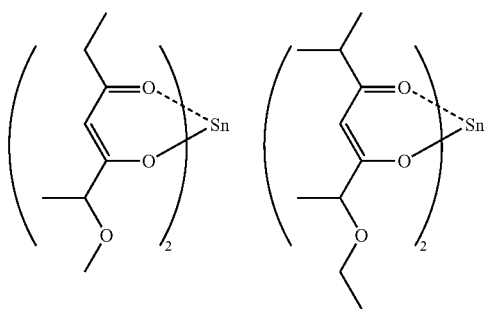
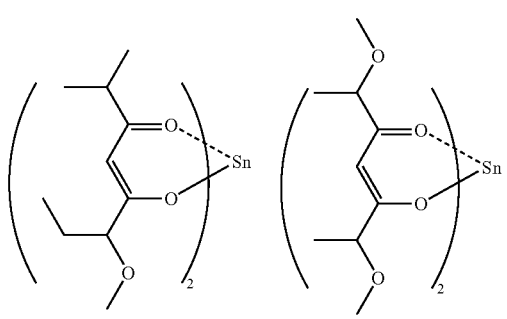
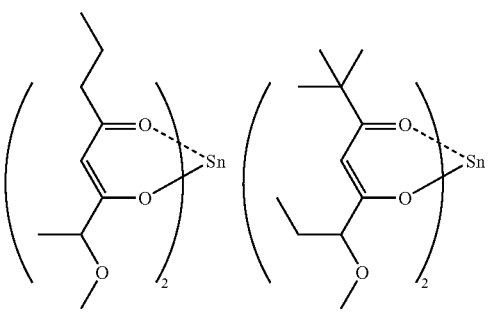
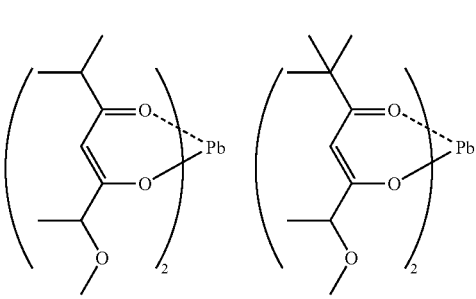
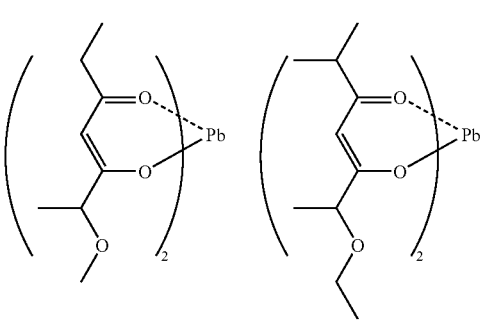
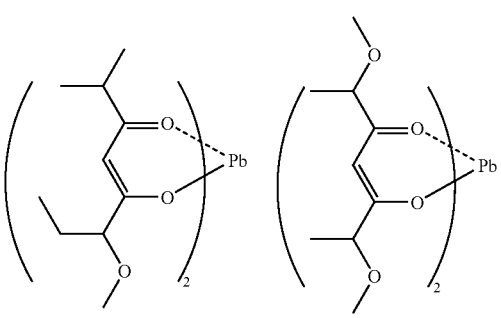
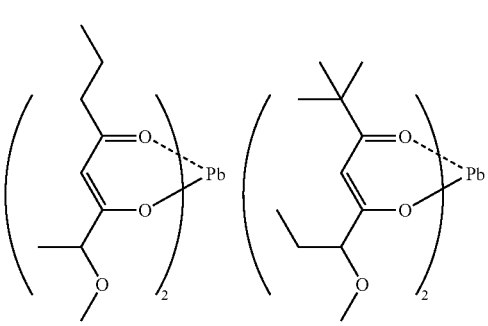

-continued
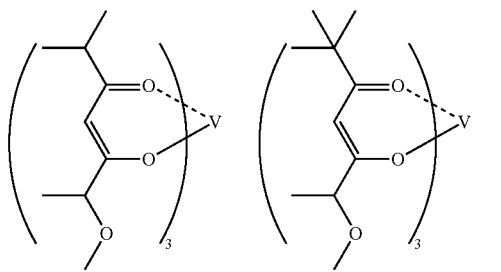
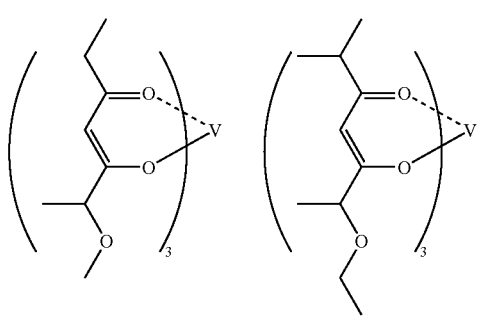
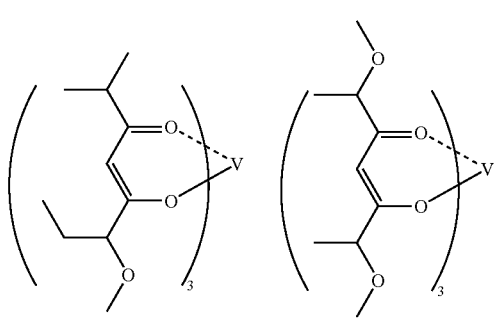
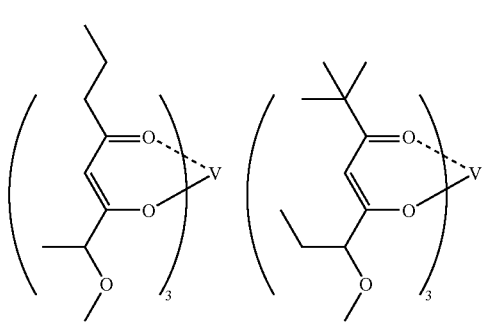
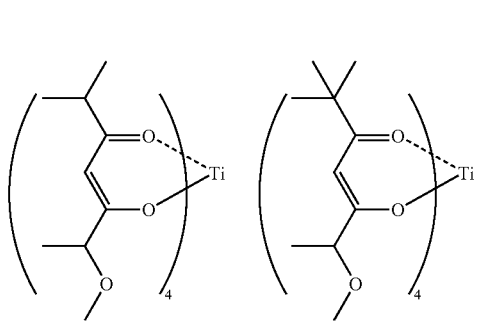
-continued
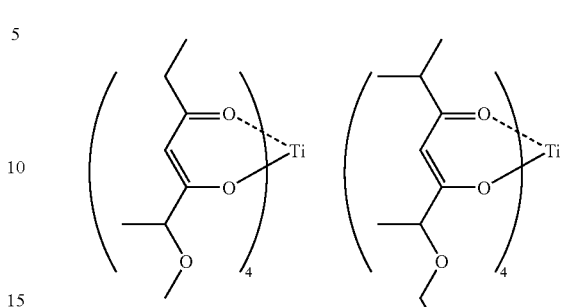
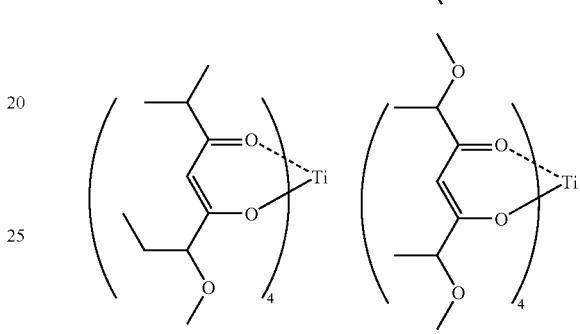
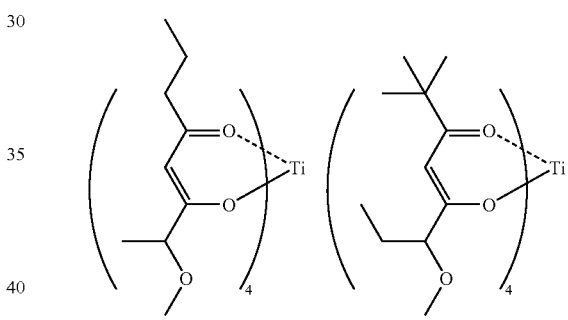
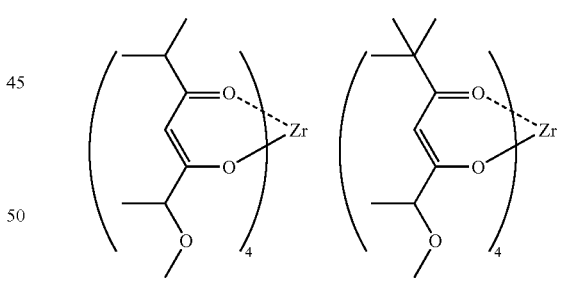
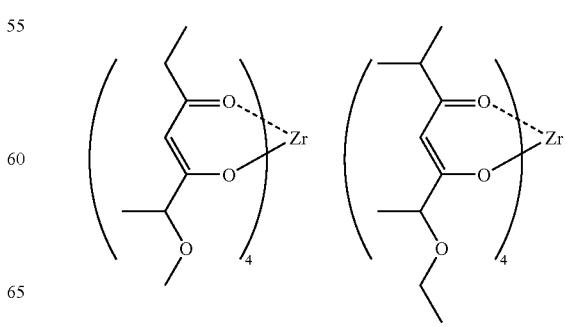

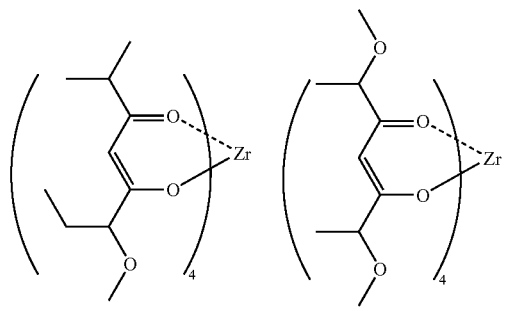
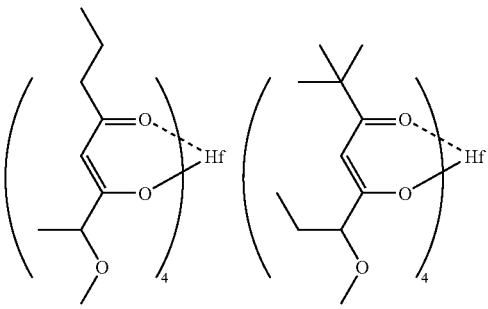
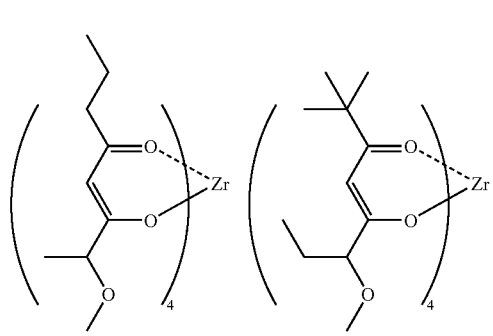
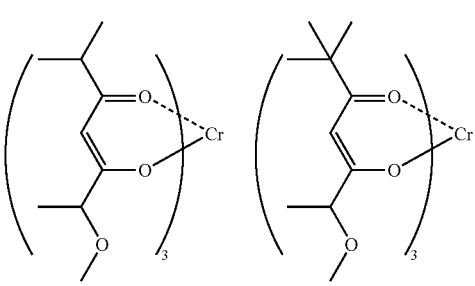
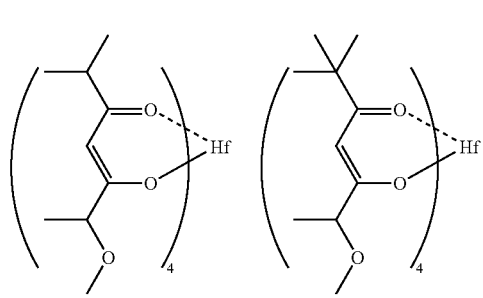
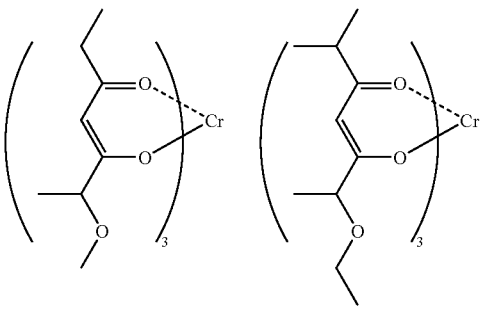
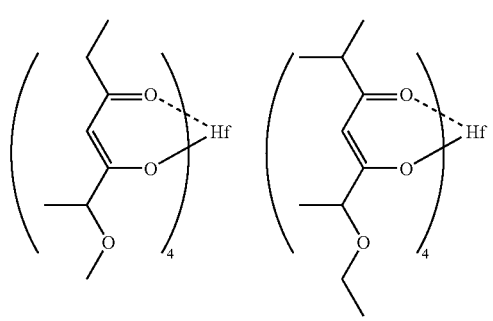
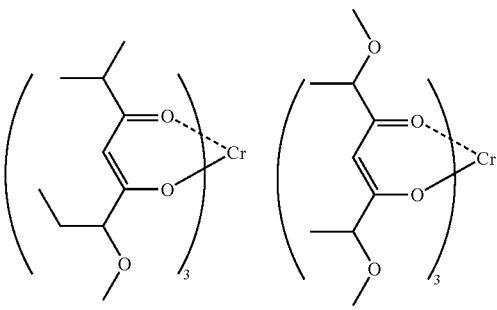
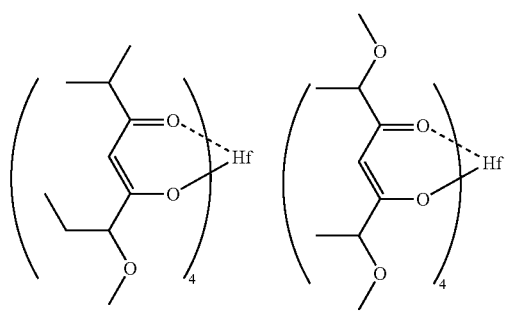
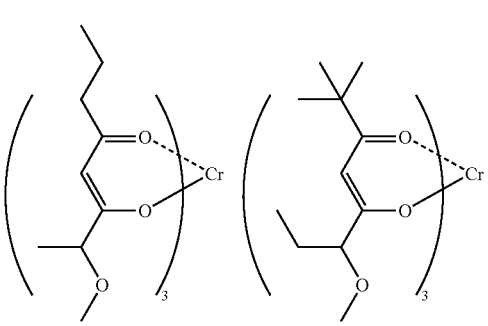

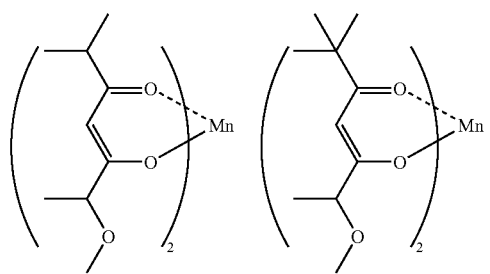
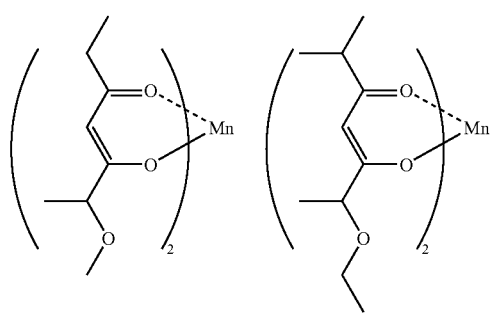
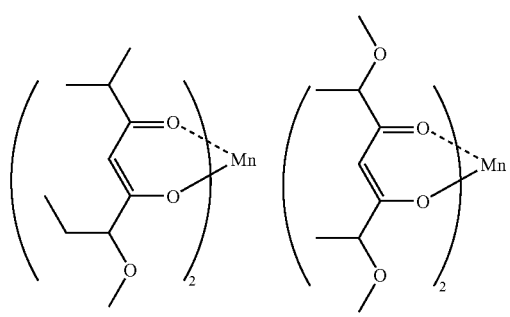
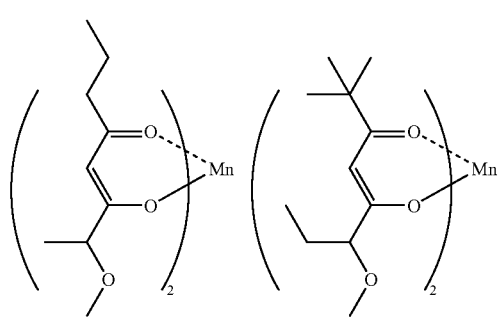
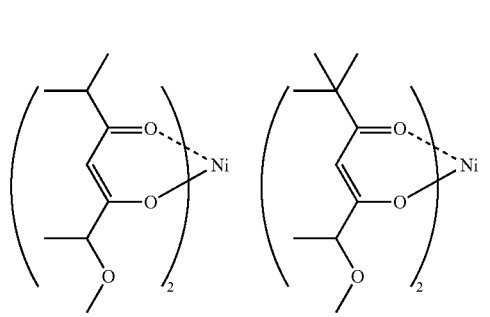
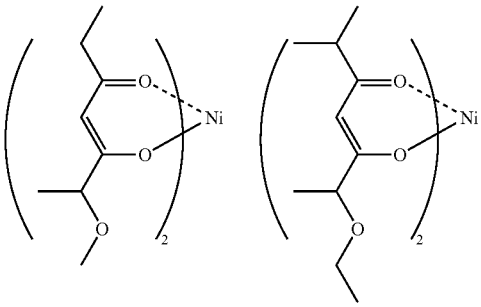
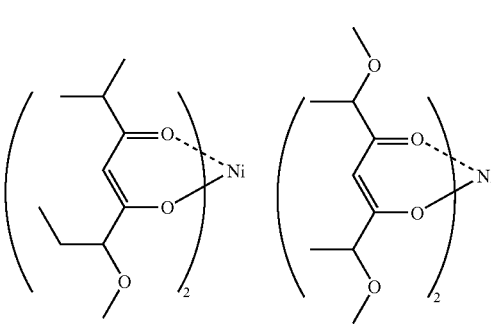
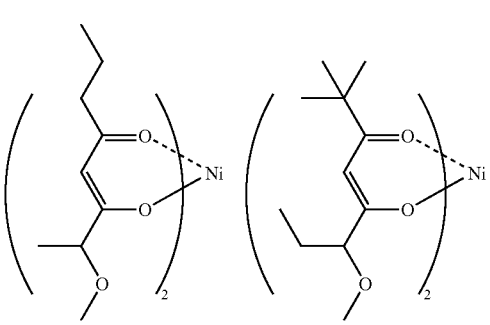
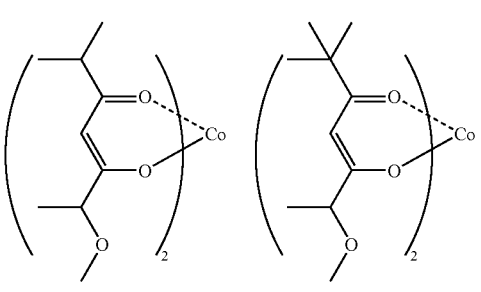
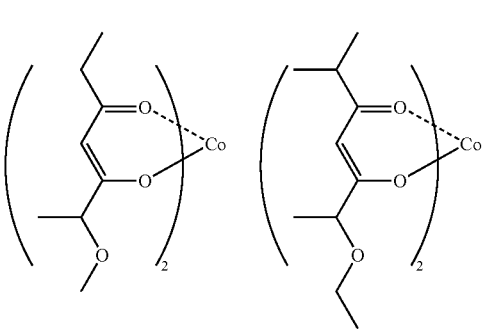

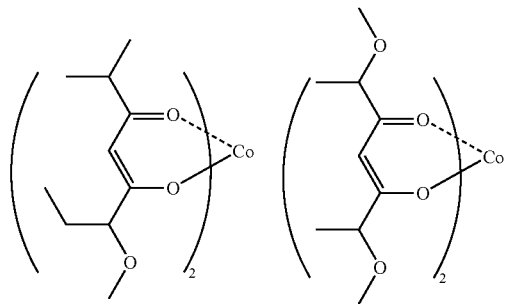
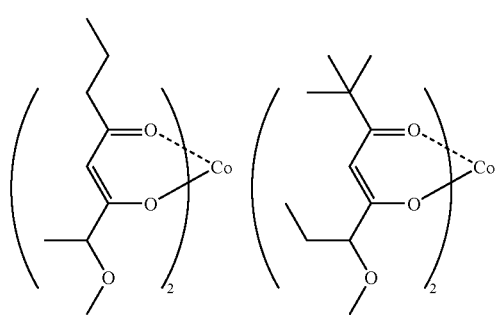
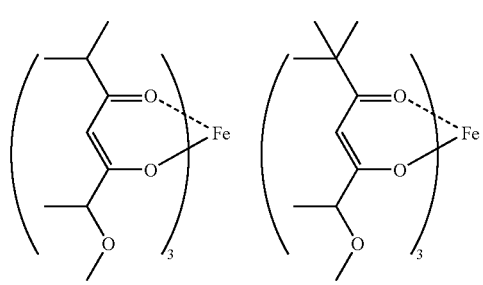
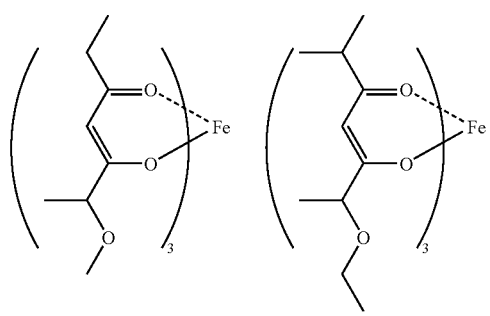
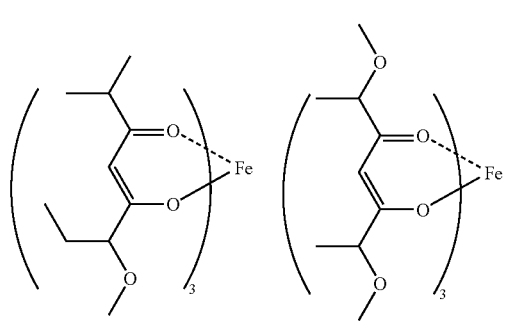
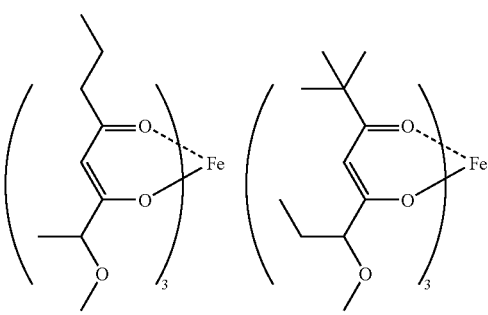
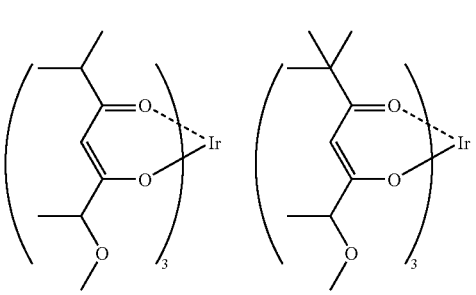
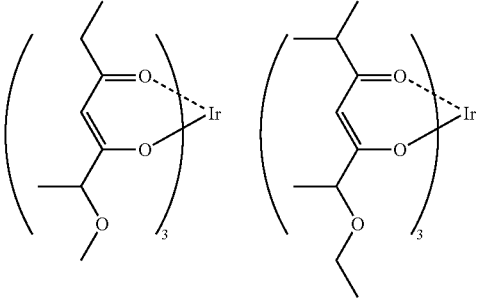
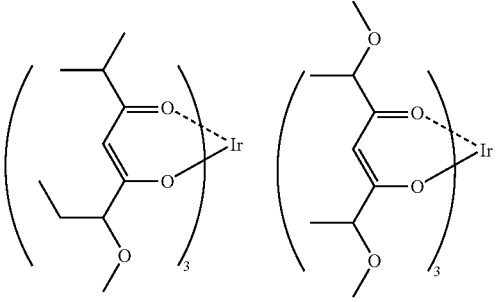
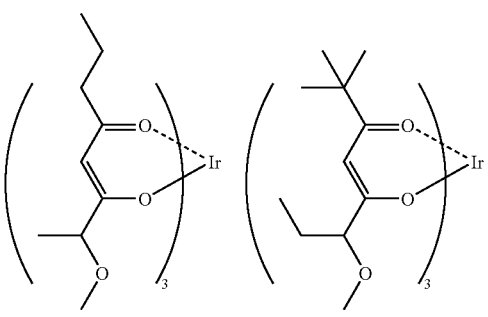

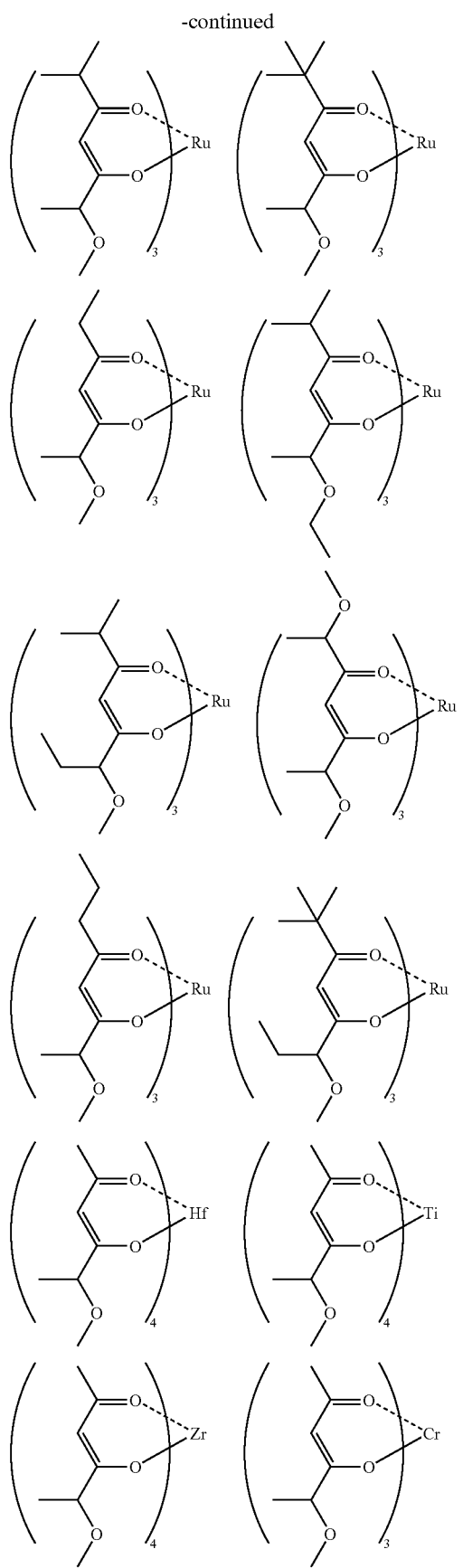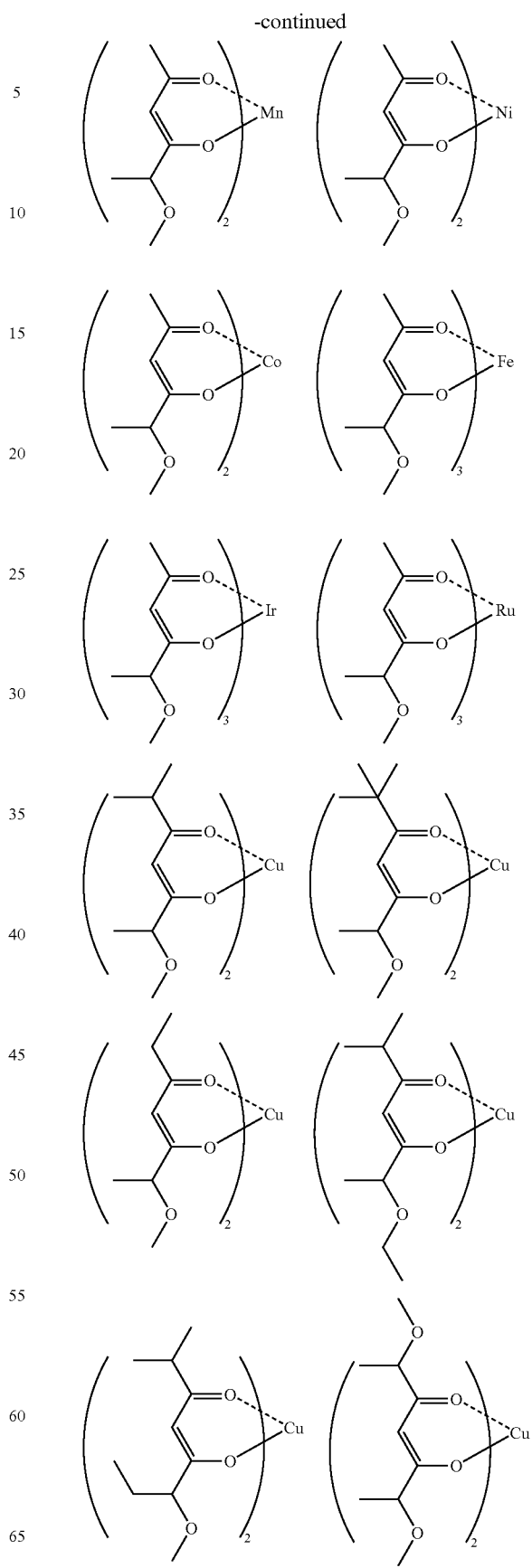

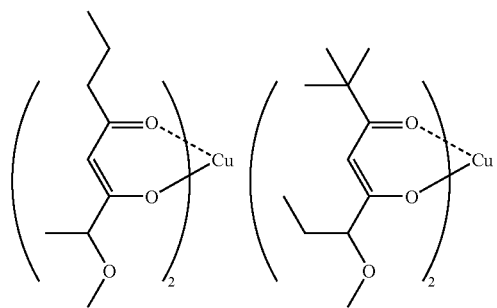
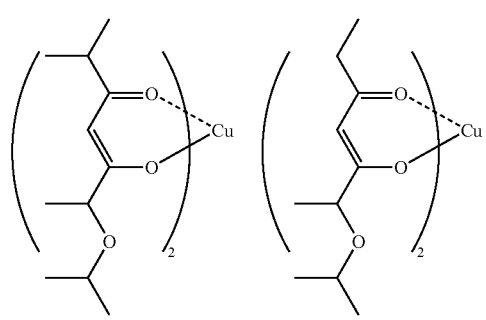
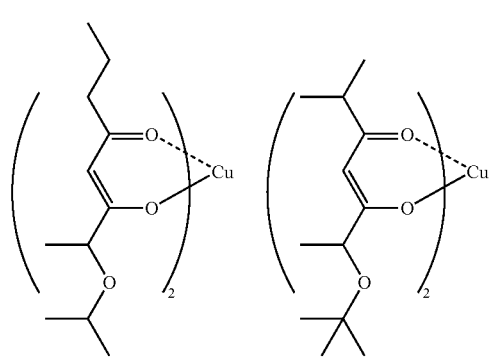
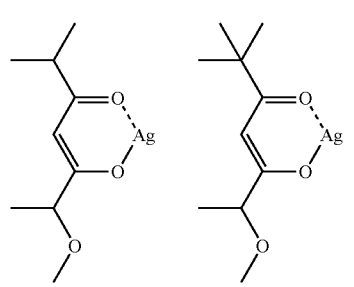
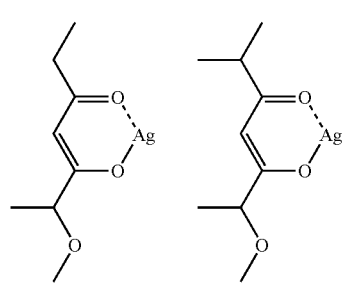
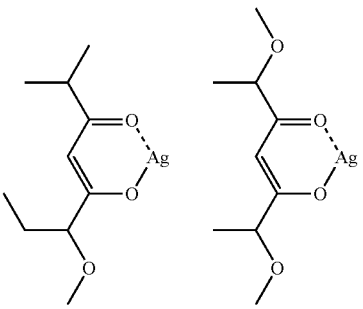
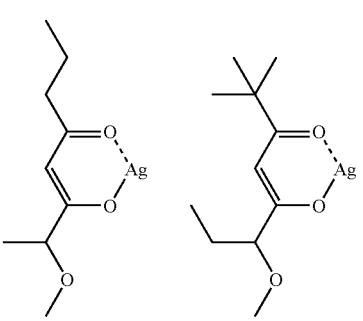
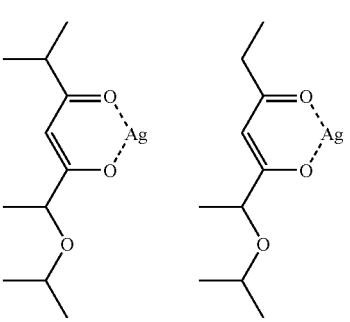
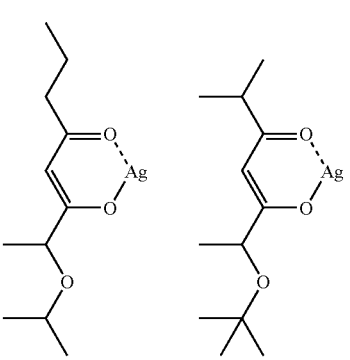
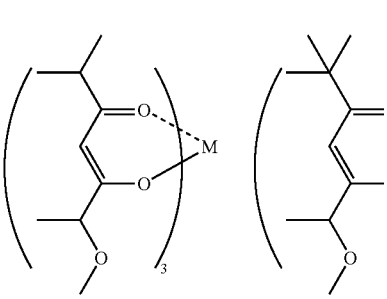

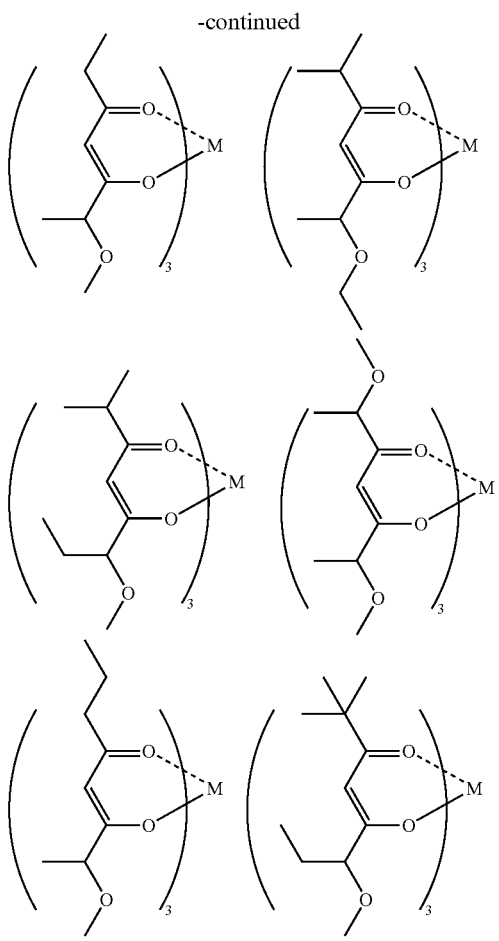

[in the formulas, M is a rare earth metal].

The deposition of the metal-containing compound onto the substrate can be carried out by the known CVD method. For instance, the metal complex compound is supplied onto a heated substrate together with an oxidizing gas such as oxygen, ozone, nitrogen oxide (e.g., $N_2O$) or a reducing gas such as hydrogen under atmospheric or reduced pressure, to deposit an metal oxide film or a metal film on the substrate. Alternatively, a metal complex compound is supplied onto a heated substrate together with a nitrogen-containing basic gas such as ammonia to deposit a metal nitride film on the substrate. Otherwise, a metal-containing film is deposited on a substrate by a plasma CVD method.

The process for preparing a metal oxide film by the CVD method can be performed by a step of heating a metal complex compound of the invention to give a vapor of the metal complex compound and supplying the vapor into a reaction chamber in which a substrate is placed and a subsequent step of bringing the vapor into contact with oxygen or stream (i.e., water vapor) in the reaction chamber under heating to decompose the vapor to convert into a metal oxide vapor and depositing the metal oxide vapor on a surface of the substrate.

The process for preparing a metal film by the CVD method can be performed by a step of heating a metal complex compound of the invention to give a vapor of the metal complex compound and supplying the vapor into a reaction chamber in which a substrate is placed and a subsequent step of bringing the vapor into contact with hydrogen in the reaction chamber under heating to decompose the vapor to convert into a metal vapor and depositing the metal vapor on a surface of the substrate.

In the CVD method, the metal complex compound is vaporized for the formation of a thin film. The metal complex compound of the invention can be supplied into a vaporizing chamber and vaporized in the chamber. Alternatively, the metal complex compound is diluted with an appropriate solvent (for example, an aliphatic hydrocarbon such as hexane or octane; an aromatic hydrocarbon such as toluene; or an ether such as tetrahydrofuran or dibutyl ether) and the resulting solution is supplied into the vaporizing chamber using a liquid-transporting pump and vaporized in the chamber (namely, a solution method).

The metal complex compound of the invention can be converted into a metal-containing film in a reaction chamber at a temperature of preferably 50 to 700° C., more preferably 100 to 500° C. and at a pressure of preferably 1 to 200 kPa, more preferably 10 to 110 kPa. The metal complex compound can be vaporized at a temperature of preferably 50 to 250° C., more preferably 90 to 200° C.

When a metal oxide film is deposited using an oxidizing gas such as oxygen, the oxidizing gas is used in an amount of preferably 10 to 90 vol. %, more preferably 20 to 70 vol. %, per a total amount of the gaseous mixture. When a metal oxide film is deposited using steam, the steam is used in an amount of preferably 5 to 90 vol. %, more preferably 10 to 70 vol. %, per a total amount of the gaseous mixture. When a metal film is deposited using a reducing gas such as hydrogen, the reducing gas is used in an amount of preferably 10 to 95 vol. %, more preferably 30 to 90 vol. %, per a total amount of the gaseous mixture. When a metal film is deposited using a nitrogen-containing basic gas such as ammonia, the nitrogen containing gas is used in an amount of preferably 10 to 95 vol. %, more preferably 20 to 90 vol. %, per a total amount of the gaseous mixture.

EXAMPLES

Reference Example 1

Preparation of methyl 2-methoxypropionate

In a 500 mL-volume flask equipped with a stirrer, a thermometer and a dropping funnel were placed 100.6 g (1,862 mmol) of sodium methoxide and 300 mL of hexane. Subsequently, 300.3 g (1,798 mmol) of methyl 2-bromopropionate was slowly dropped into the flask under cooling with ice. The resulting mixture was stirred for 2 hours for carrying out a reaction. After the reaction was complete, 300 mL of water was added to the reaction mixture under cooling with ice. The organic portion was collected, washed with water, and dried over anhydrous sodium sulfate. The dried organic portion was filtered and placed under reduced pressure to distill at 74° C. and 12,236 Pa, to give 97.0 g (yield: 46%) of methyl 2-methoxypropionate as colorless liquid.

The methyl 2-methoxypropionate had the following characteristics:

$^1$H-NMR (CDCl$_3$, δ (ppm)): 1.41 (3H, d), 3.40 (3H, s), 3.77 (3H, s), 3.90 (1H, q), MS (m/e): 88.59, 31.15.

Reference Example 2

Preparation of 2-methoxy-6-methyl-3,5-heptanedione (mopd)

In a 200 mL-volume flask equipped with a stirrer, a thermometer and a dropping funnel was placed 5.15 g (132 mmol) of sodium amide, and the flask was purged with argon.

Then, 80 mL of toluene was placed in the flask. Subsequently, 12.0 g (139.3-mmol) of 3-methyl-2-butanone was slowly dropped into the flask, and the resulting mixture was stirred for 15 minutes. Into the flask was further dropped 5.65 g (47.8 mmol) of methyl 2-methoxy-propionate (prepared by the method of Reference Example 1), and the mixture was stirred for 30 minutes for carrying out a reaction. After the reaction was complete, 50 mL of water was placed in the flask under cooling with ice. The aqueous portion was taken out, neutralized with acetic acid, and subjected to extraction with ether. The ether extract was washed with water, dried over anhydrous sodium sulfate, and filtered. The filtrate was concentrated and distilled under reduced pressure (41° C., 27 Pa) to give 4.25 g (yield: 52%) of 2-methoxy-6-methyl-3,5-heptanedione as colorless liquid.

The 2-methoxy-6-methyl-3,5-heptanedione had the following characteristics:

$^1$H-NMR (CDCl$_3$, δ (ppm)): 1.17 (6H, d), 1.30 (0.15H, d), 1.36 (2.85H, d), 2.48-2.57 (0.95H, m), 2.59-2.73 (0.05H, m), 3.36 (0.15H, s), 3.37 (2.85H, s), 3.71-3.78 (1H, m), 3.78 (0.1H, s), 5.81 (0.95H, s), 15.4 (0.95H, s), IR (neat, cm$^{-1}$): 2976, 2936, 1607 (br), 1462, 1366, 1328, 1210, 1120, 910, 805 (the peak at 1607 cm$^{-1}$ is a characteristic peak of β-diketone), MS (m/e): 142, 113, 59, 43.

Reference Example 3

Preparation of 2-methoxy-6,6-dimethyl-3,5-heptanedione (mobd)

In a 200 mL-volume flask equipped with a stirrer, a thermometer and a dropping funnel was placed 8.20 g (210 mmol) of sodium amide, and the flask was purged with argon. Then, 80 mL of toluene was placed in the flask. Subsequently, 15.1 g (150.8 mmol) of 3,3-dimethyl-2-butanone was slowly dropped into the flask, and the resulting mixture was stirred for 15 minutes. Into the flask was further dropped 5.50 g (46.6 mmol) of methyl 2-methoxypropionate (prepared by the method of Reference Example 1), and the mixture was stirred for 30 minutes for carrying out a reaction. After the reaction was complete, 50 mL of water was placed in the flask under cooling with ice. The aqueous portion was taken out, neutralized with acetic acid, and subjected to extraction with ether. The ether extract was washed with water, dried over anhydrous sodium sulfate, and filtered. The filtrate was concentrated and distilled under reduced pressure (59° C., 492 Pa) to give 4.50 g (yield: 52%) of 2-methoxy-6,6-dimethyl-3,5-heptanedione as colorless liquid.

The 2-methoxy-6,6-dimethyl-3,5-heptanedione had the following characteristics:

$^1$H-NMR (CDCl$_3$, δ (ppm)): 1.18 (0.99H, s), 1.20 (8.01H, s), 1.35 (0.33H, d), 1.37 (2.67H, d), 3.35 (0.33H, s), 3.37 (2.67H, s), 3.73-3.77 (1H, m), 3.79 (0.22H, s), 5.91 (0.89H, s), 15.7 (0.89H, s), IR (neat, cm$^{-1}$): 2972, 2936, 1602 (br), 1461, 1366, 1200, 1059, 886, 809 (the peak at 1602 cm$^{-1}$ is a characteristic peak of β-diketone), MS (m/e): 186, 156, 127, 59, 43.

Example A-1

Preparation of tris(2-methoxy-6-methyl-3,5-heptanedionato)indium(III)—In(mopd)$_3$ In a 100 mL-volume flask equipped with a stirrer, a thermometer and a dropping funnel was placed 4.26 g (22.1 mmol) of 28% sodium methoxide methanol solution. Into the ice-cooled solution was slowly dropped 3.80 g (22.1 mmol) of 2-methoxy-6-methyl-3,5-heptanedione (prepared by the method of Reference Example 2), and the mixture was stirred for 5 minutes. Subsequently, a solution of 2.04 g (6.96 mmol) of indium(III) chloride tetrahydrate in 15 mL of methanol was slowly added to the mixture. The resulting mixture was stirred for 30 minutes under cooling with ice for carrying out a reaction. After the reaction was complete, the reaction mixture was placed under reduced pressure to distill methanol off. To the residue were added 40 mL of ether and 40 mL of water. The organic portion was taken out, dried over anhydrous sodium sulfate, and filtered. The filtrate was concentrated. The concentrated filtrate was placed under reduced pressure and distilled at 175° C., 31 Pa, to give 3.27 g (yield: 74%) of tris(2-methoxy-6-methyl-3,5-heptanedionato) indium(III) as viscous yellow liquid.

The tris(2-methoxy-6-methyl-3,5-heptanedione-indium (III) is a new compound having the following characteristics:

IR (neat, cm$^-$): 2975, 2933, 1571, 1539, 1515, 1429, 1402, 1363, 1331, 1230, 1120, 952, 914, 809, 554 (the characteristic peak (1607 cm$^{-1}$) of β-diketone has disappeared, and a characteristic peak (1571 cm$^{-1}$) of β-diketonato appears), Elemental analysis: found: C, 51.3%; H, 7.25%; In, 18%. calculated (C$_{27}$H$_{45}$O$_9$In): C, 51.6%; H, 7.22%; In, 18.3%. MS (m/e): 628, 598, 457, 227, 115, 59.

Example A-2

Preparation of tris(2-methoxy-6,6-dimethyl-3,5-heptanedionato)indium(III)—In(mobd)$_3$ In a 100 mL-volume flask equipped with a stirrer, a thermometer and a dropping funnel was placed 2.12 g (11.0 mmol) of 28% sodium methoxide methanol solution. Into the ice-cooled solution was slowly dropped 2.03 g (10.9 mmol) of 2-methoxy-6,6-dimethyl-3,5-heptanedione (prepared by the method of Reference Example 3), and the mixture was stirred for 5 minutes. Subsequently, a solution of 1.08 g (3.68 mmol) of indium(III) chloride tetra-hydrate in 15 mL of methanol was slowly added to the mixture. The resulting mixture was stirred for 30 minutes under cooling with ice for carrying out a reaction. After the reaction was complete, the reaction mixture was placed under reduced pressure to distill methanol off. To the residue were added 40 mL of ether and 40 mL of water. The organic portion was taken out, dried over anhydrous sodium sulfate, and filtered. The filtrate was concentrated. The concentrated filtrate was placed under reduced pressure and distilled at 180° C., 37 Pa, to give 1.56 g (yield: 63%) of tris(2-methoxy-6,6-dimethyl-3,5-heptanedionato) indium(III) as pale yellow solid.

The tris(2-methoxy-6,6-dimethyl-3,5-heptanedionato)-indium(III) is a new compound having the following characteristics:

mp: 76° C., IR (KBr, cm$^{-1}$): 2975, 2932, 1565, 1516, 1420, 1383, 1359, 1214, 1163, 1117, 1057, 953, 888, 813, 553, 481 (the characteristic peak (1602 cm$^{-1}$) of β-diketone has disappeared, and a characteristic peak (1565 cm$^{-1}$) of β-diketonato appears), Elemental analysis: found: C, 53.8%; H, 7.69%; In, 17%. calculated (C$_{30}$H$_{51}$O$_9$In): C, 53.7%; H, 7.67%; In, 17.1%. MS (m/e): 670, 640, 613, 485, 243, 127, 59.

Example A-3

Preparation of bis(2-met-6-methyl-3,5-heptanedionato)strontium(II)—Sr(mopd)$_2$

In a 100 mL-volume flask equipped with a stirrer, a thermometer and a dropping funnel were placed 0.60 g (5.79 mmol) of strontium(II) oxide and 20 mL of ether. Into the ice-cooled solution were slowly dropped 40 mg of water and 2.00 g (11.61 mmol) of 2-methoxy-6-methyl-3,5-heptanedione (prepared by the method of Reference Example 2), and the mixture was stirred for one hour for carrying out a reaction. After the reaction was complete, the reaction mixture was placed under reduced pressure and heated to 180° C. for concentration. To the concentrate was added 15 mL of hexane. The resulting mixture was stirred and then filtered. The filtrate was concentrated and distilled under reduced pressure (240° C., 53 Pa), to give 0.20 g (yield: 8%) of bis(2-methoxy-6-methyl-3,5-heptanedionato)strontium(II) as pale yellow solid.

The bis(2-methoxy-6-methyl-3,5-heptanedionato)-strontium(II) is a new compound having the following characteristics:

IR (KBr, cm$^{-1}$): 3421, 2970, 2932, 1614, 1499, 1464, 1435, 1374, 1347, 1208, 1150, 1117, 1089, 1020, 911, 809, 782, 548, 520, 480,

Elemental analysis: found: C, 50.6%; H, 7.06%; Sr, 20%. calculated ($C_{18}H_{30}O_6Sr$): C, 50.3%; H, 7.03%; Sr, 20.4%. MS (m/e): 1119, 883, 689, 537, 474, 259, 113, 59, 43.

From the MS data, the strontium complex compound is considered to have a trimer structure.

Example A-4

Preparation of bis(2-methoxy-6,6-dimethyl-3,5-heptanedionato)strontium(II)—Sr(mobd)$_2$ In a 100 mL-volume flask equipped with a stirrer, a thermometer and a dropping funnel were placed 0.58 g (5.60 nm ml) of strontium(II) oxide and 20 mL of ether. Into the ice-cooled solution were slowly dropped 40 mg of water and 2.10 g (11.28 mmol) of 2-methoxy-6,6-dimethyl-3,5-heptanedione (prepared by the method of Reference Example 3), and the mixture was stirred for one hour for carrying out a reaction. After the reaction was complete, the reaction mixture was placed under reduced pressure and heated to 180° C. for concentration. To the concentrate was added 15 mL of hexane. The resulting mixture was stirred and then filtered. The filtrate was concentrated and distilled under reduced pressure (275° C., 32 Pa), to give 0.65 g (yield: 25%) of bis(2-methoxy-6,6-dimethyl-3,5-heptanedionato)strontium(II) as pale yellow solid.

The bis(2-methoxy-6,6-dimethyl-3,5-heptanedionato)-strontium(II) is a new compound having the following characteristics:

mp: 130° C., IR (KBr, (cm$^{-2}$)): 3430, 2970, 2903, 1609, 1502, 1473, 1434, 1344, 1206, 1151, 1104, 1055, 1018, 884, 839, 784, 751, 474,

Elemental analysis: found: C, 52.6%; H, 7.51%; Sr, 19%. calculated ($C_{20}H_{34}O_6Sr$): C, 52.4%; H, 7.48%; Sr, 19.1%. MS (m/e): 1189, 731, 273.

Example A-5

Preparation of bis(2-methoxy-6-methyl-3,5-heptanedionato)zinc(II)—Zn(mopd)$_2$

In a 50 mL-volume flask equipped with a stirrer, a thermometer and a dropping funnel was placed 6.56 g (34.01 mmol) of 28% sodium methoxide methanol solution. Into the ice-cooled solution was slowly dropped 6.00 g (34.8 mmol) of 2-methoxy-6-methyl-3,5-heptanedione (prepared by the method of Reference Example 2), and the mixture was stirred for 5 minutes. Subsequently, a solution of 2.26 g (16.6 mmol) of zinc(II) chloride in 20 mL of methanol was slowly added to the mixture. The resulting mixture was stirred for 30 minutes under cooling with ice for carrying out a reaction. After the reaction was complete, the reaction mixture was placed under reduced pressure to distill methanol off. To the residue were added 20 mL of hexane and 20 mL of water. The organic portion was taken out, dried over anhydrous sodium sulfate, fate, and filtered. The filtrate was concentrated. The concentrated filtrate was placed under reduced pressure and distilled at 160° C., 27 Pa, to give 4.91 g (yield: 73%) of bis(2-methoxy-6-methyl-3,5-heptanedionato)zinc(II) as viscous yellow liquid.

The bis(2-methoxy-6-methyl-3,5-heptanedionato)-zinc (II) is a new compound having the following characteristics:

IR (neat, cm$^{-1}$): 2972, 2932, 1582, 1513, 1432, 1333, 1211, 1118, 912, 805, 558 (the characteristic peak (1607 cm$^{-1}$) of β-diketone has disappeared, and a characteristic peak (1582 cm$^{-1}$) of β-diketonato appears), Elemental analysis: found: C, 53.1%; H, 7.45%; Zn, 16%. calculated ($C_{18}H_{30}O_6Zn$): C, 53.0%; H, 7.41%; Zn, 16.0%. MS (m/e): 641, 406.

From the MS data, the zinc complex compound is considered to have a dimer structure.

Example A-6

Preparation of bis(2-methoxy-6-methyl-3,5-heptanedionato)tin(II)—Sn(mopd)$_2$

In a 100 mL-volume flask equipped with a stirrer, a thermometer and a dropping funnel was placed 4.70 g (24.4 mmol) of 28% sodium methoxide methanol solution. Into the ice-cooled solution was slowly dropped 4.30 g (25.0 mmol) of 2-methoxy-6-methyl-3,5-heptanedione (prepared by the method of Reference Example 2), and the mixture was stirred for 5 minutes. Subsequently, a solution of 2.25 g (11.9 mmol) of tin(II) chloride in 10 mL of methanol was slowly added to the mixture. The resulting mixture was stirred for 30 minutes under cooling with ice for carrying out a reaction. After the reaction was complete, the reaction mixture was placed under reduced pressure to distill methanol off. To the residue was added 30 mL of hexane, and the resulting mixture was filtered. The filtrate was concentrated. The concentrated filtrate was placed under reduced pressure and distilled at 146° C., 31 Pa, to give 4.36 g (yield: 77%) of bis(2-methoxy-6-methyl-3,5-heptanedionato)tin(II) as yellow liquid.

The bis(2-methoxy-6-methyl-3,5-heptanedionato)-tin(II) is a new compound having the following characteristics:

IR (neat, cm$^{-1}$): 2974, 2932, 1573, 1511, 1411, 1327, 1210, 1119, 953, 912, 808, 545 (the characteristic peak (1607 cm$^{-1}$) of β-diketone has disappeared, and a characteristic peak (1573 cm$^{-1}$) of β-diketonato appears), Elemental analysis: found: C, 46.8%; H, 6.61%; Sn, 25.6%; calculated ($C_{18}H_{30}O_6Sn$): C, 46.9%; H, 6.56%; Sn, 25.7%. MS (m/e): 462, 403, 291, 151, 113, 59.

Example A-7

Preparation of tris(2-methoxy-6-methyl-3,5-heptanedionato)vanadium(III)—V(mopd)$_3$ In a 100 mL-volume flask equipped with a stirrer, a thermometer and a dropping funnel was placed 3.61 g (18.7 mmol) of 28% sodium methoxide methanol solution. Into the ice-cooled solution was slowly dropped 3.20 g (18.6 mmol) of 2-methoxy-6-methyl-3,5-heptanedione (prepared by the method of Reference Example 2), and the mixture was stirred for 5 minutes. Subsequently, a solution of 0.93 g (5.91 mmol) of vanadium(III) chloride in 15 mL of methanol was slowly added to the mixture. The resulting mixture was stirred for 30 minutes under cooling with ice for carrying out a reaction. After the reaction was complete, the reaction mixture was placed under reduced pressure to distill methanol off. To the residue were added 30 mL of hexane and 30 mL of water. The organic portion was taken out, dried over anhydrous sodium sulfate, and filtered. The filtrate was concentrated. The concentrated filtrate was placed under reduced pressure and distilled at 180° C., 44 Pa, to give 2.65 g (yield: 79*) of tris(2-methoxy-6-methyl-3,5-heptanedionato)vanadium-(III) as viscous brown liquid.

The tris(2-methoxy-6-methyl-3,5-heptanedionato)-vanadium(III) is a new compound having the following characteristics:

IR (neat, cm$^{-1}$): 2975, 2933, 1563, 1511, 1411, 1330, 1211, 1121, 1008, 913, 805, 561 (the characteristic peak (1607 cm$^{-1}$) of β-diketone has disappeared, and a characteristic peak (1563 cm$^{-1}$) of β-diketonato appears), Elemental analysis: found: C, 57.3%; H, 8.05%; V, 9.0%. calculated ($C_{27}H_{45}O_9V$): C, 57.4%; H, 8.03%; V, 9.02%. MS (m/e): 564, 393, 59.

Example A-8

Preparation of tris(2-methoxy-6-methyl-3,5-heptanedionato)aluminum(III)—Al(mopd)$_3$ In a 100 mL-volume flask equipped with a stirrer, a thermometer and a dropping funnel were placed 1.07 g (6.60 mmol) of aluminum(III) triethoxide and 4.20 g (24.4 mmol) of 2-methoxy-6-methyl-3,5-heptanedione (prepared by the method of Reference Example 2). The resulting mixture was heated to 150° C. for carrying out a reaction with distillation of ethanol. After the reaction was complete, 20 mL of hexane and 20 mL of water were added. The organic portion was taken out, dried over anhydrous sodium sulfate, and filtered. The filtrate was concentrated. The concentrated filtrate was placed reduced pressure and distilled at 160° C., 27 Pa, to give 3.41 g (yield: 96%) of tris(2-methoxy-6-methyl-3,5-heptanedionato)aluminum(III) as pale yellow liquid.

The tris(2-methoxy-6-methyl-3,5-heptanedionato)-aluminum(III) is a new compound having the following characteristics:

IR (neat, cm$^{-1}$): 2975, 2933, 1583, 1536, 1457, 1420, 1247, 1211, 1121, 915, 799, 565 (the characteristic peak (1607 cm$^{-1}$) of β-diketone has disappeared and a characteristic-peak (1583 cm$^{-1}$) of β-diketonato appears), Elemental analysis: found: C, 60.1%; H, 8.41%; Al, 5.0%; calculated ($C_{27}H_{45}O_9Al$): C, 60.0%; H, 8.39%; Al, 4.99%. MS (m/e): 540, 510, 481, 369, 197, 59.

Example A-9

Preparation of bis(2-methoxy-6-methyl-3,5-heptanedionato)magnesium(II)—Mg(mopd)$_2$ In a 100 mL-volume flask equipped with a stirrer, a thermometer and a dropping funnel were placed 0.66 g (11.3 mmol) of magnesium(II) hydroxide and 15 mL of 1,2-dimethoxyethane. Subsequently, 40 mL of water and 4.30 g (25.0 mmol) of 2-methoxy-6-dimethyl-3,5-heptanedione (prepared by the method of Reference Example 3) were successively and slowly dropped. The resulting mixture was stirred for carrying out a reaction. After the reaction was complete, the reaction mixture was concentrated by heating under reduced pressure. The concentrate was placed under reduced pressure and distilled at 210° C., 25 Pa, to give 3.75 g (yield: 90%) of bis(2-methoxy-6-dimethyl-3,5-heptanedionato)magnesium(II) as pale yellow glassy solid.

The bis(2-methoxy-6-methyl-3,5-heptanedionato)-magnesium(II) is a new compound having the following characteristics:

m.p.: 41° C. IR (KBr, cm$^{-1}$): 3421 (br), 2972, 2933, 1613, 1526, 1437, 1334, 1218, 1150, 1117, 912, 803, 564,

Elemental analysis: found: C, 59.0%; H, 8.28%; Mg, 6.6%; calculated ($C_{18}H_{30}O_6Mg$): C, 59.0%; H, 8.25%; Mg, 6.63%. MS (m/e): 561, 398, 366, 323, 113, 59.

From the MS data, the magnesium complex compound is considered to have a dimer structure.

Example A-10

Preparation of bis(2-methoxy-6-methyl-3,5-heptanedionato)lead(II)—Pb(mopd)$_2$

In a 100 mL-volume flask equipped with a stirrer, a thermometer and a dropping funnel was placed 4.50 g (23.3 mmol) of 28% sodium methoxide methanol solution. Into the ice-cooled solution was slowly dropped 4.10 g (23.8 mmol) of 2-methoxy-6-methyl-3,5-heptanedione (prepared by the method of Reference Example 2), and the mixture was stirred for 5 minutes. Subsequently, 3.20 g (11.5 mmol) of lead(II) chloride was slowly added to the mixture. The resulting mixture was stirred for one hour at room temperature for carrying out a reaction. After the reaction was complete, the reaction mixture was placed under reduced pressure to distill methanol off. To the residue were added 30 mL of hexane and 30 mL of water. The organic portion was taken out, dried over anhydrous sodium sulfate, and filtered. The filtrate was concentrated. The concentrated filtrate was placed under reduced pressure and distilled at 185° C., 23 Pa, to give 5.00 g (yield: 79%) of bis(2-methoxy-6-methyl-3,5-heptanedionato)lead-(II) as viscous yellow liquid.

The bis(2-methoxy-6-methyl-3,5-heptanedionato)-lead (II) is a new compound having the following characteristics:

IR (neat, cm$^{-1}$): 2970, 2930, 1595, 1504, 1423, 1327, 1208, 1151, 1116, 1016, 947, 910, 800, 539 (the characteristic peak (1607 cm$^{-1}$) of β-diketone has disappeared, and a characteristic peak (1595 cm$^{-1}$) of β-diketonato appears), Elemental analysis: found: C, 39.0%; H, 5.51%; Pb, 37.8%; calculated ($C_{18}H_{30}O_6Pb$): C, 39.3%; H, 5.50%; Pb, 37.7%. MS (m/e): 550, 491, 379, 59.

Example A-11

Preparation of bis(2-methoxy-6,6-dimethyl-3,5-heptanedionato)barium(III)—Ba (mobd)$_2$ In a 100 mL-volume flask equipped with a stirrer, a thermometer and a dropping funnel were placed 1.84 g (10.7 mmol) of anhydrous barium(II) hydroxide and 40 mL of 1,2-dimethoxyethane. Subsequently, 4.00 g (21.5 mmol) of 2-methoxy-6,6-dimethyl-3,5-heptanedione (prepared by the method of Reference Example 3) were slowly dropped. The resulting mixture was stirred at room temperature for carrying out a reaction. After the reaction was complete, the reaction mixture was concentrated. To the concentrate was added 20 mL of hexane. The resulting mixture was filtered. The filtrate was concentrated. The concentrate was placed under reduced pressure and distilled at 270° C., 73 Pa, to give 1.25 g (yield: 23%) of bis(2-methoxy-6,6-dimethyl-3,5-heptanedionato)barium(II) as orange solid.

The bis(2-methoxy-6,6-dimethyl-3,5-heptanedionato)-barium(II) is a new compound having the following characteristics:

m.p.: 105° C. IR (KBr, cm$^{-1}$): 3433, 2970, 2902, 1606, 1473, 1434, 1344, 1153, 1105, 1017, 839, 783, 472,

Elemental analysis: found: C, 47.5%; H, 6.80%; Ba, 27%. calculated ($C_{20}H_{34}O_6Ba$): C, 47.3%; H, 6.75%; Ba, 20.0%. MS (m/e): 831, 717, 426, 127, 59.

From the MS data, the barium complex compound is considered to have a dimer structure.

Example A-12

Preparation of tris(2-methoxy-6-methyl-3,5-heptanedionato)gallium (III)—Ga(mopd)$_3$ In a 100 mL-volume flask equipped with a stirrer, a thermometer and a dropping funnel was placed 4.63 g (24.0 mmol) of 28% sodium methoxide methanol solution. Into the ice-cooled solution was slowly dropped 4.14 q (24.0 mmol) of 2-methoxy-6-methyl-3,5-heptanedione (prepared by the method of Reference Example 2), and the mixture was stirred for 5 minutes. Subsequently, 1.40 g (7.95 mmol) of gallium (III) chloride was slowly added to the mixture. The resulting mixture was stirred at room temperature for one hour for carrying out a reaction. After the reaction was complete, the reaction mixture was placed under reduced pressure to distill methanol off. To the residue were added 30 mL of hexane and 30 mL of water. The organic portion was taken out, dried over anhydrous sodium sulfate, and filtered. The filtrate was concentrated. The concentrated filtrate was placed under reduced pressure and distilled at 185° C., 23 Pa, to give 4.05 g (yield: 87%) of tris(2-methoxy-6-methyl-3,5-heptanedionato)-gallium(III) as yellow liquid.

The tris(2-methoxy-6-methyl-3,5-heptanedionato)-gallium(III) is a new compound having the following characteristics:

IR (neat, cm$^{-1}$): 2976, 2934, 1577, 1537, 1436, 1408, 1363, 1331, 1240, 1211, 1121, 961, 915, 803, 562 (the characteristic peak (1607 cm$^{-1}$) of β-diketone has disappeared, and a characteristic peak (1577 cm$^{-1}$) of β-diketonato appears), Elemental analysis: found: C, 55.5%; H, 7.75%; Ga, 12%. calculated ($C_{27}H_{45}O_9Ga$): C, 55.6%; H, 7.78%; Ga, 12.0%. MS (m/e): 582, 523, 411, 59.

Reference Example 4

Preparation of 1-methoxy-5,5-dimethyl-2,4-hexanedione (mbd)

In a 200 mL-volume flask equipped with a stirrer, a thermometer and a dropping funnel was placed 9.74 g (250 mmol) of sodium amide, and the flask was purged with argon. Then, 80 mL of toluene was placed in the flask. Subsequently, 25.0 g (249.6 mmol) of 3,3-dimethyl-2-butanone was slowly dropped into the flask, and the resulting mixture was stirred for 15 minutes. Into the flask was further dropped 10.4 g (99.9 mmol) of methyl methoxyacetate, and the mixture was stirred for 30 minutes for carrying out a reaction. After the reaction was complete, 50 mL of water was placed in the flask under cooling with ice. The aqueous portion was taken out, neutralized with acetic acid, and subjected to extraction with ether. The ether extract was washed with water, dried over hydrous sodium sulfate, and filtered. The filtrate was concentrated and distilled under reduced pressure (65° C., 426 Pa) to give 5.90 g (yield: 34%) of 1-methoxy-5,5-dimethyl-2,4-hexanedione as colorless liquid.

The 1-methoxy-5,5-dimethyl-2,4-hexanedione had the following characteristics:

$^1$H-NMR(CDCl$_3$, δ (ppm)): 1.17 (1.31H, s), 1.19 (7.70H, s), 3.39 (0.44H, s), 3.43 (2.57H, s), 3.70 (0.29H, s), 4.00 (1.71H, s), 4.02 (0.29H, s), 5.90 (0.86H, s), 15.6 (0.86H, s), IR (neat, cm$^{-1}$): 2970, 2936, 1604 (br), 1465, 1365, 1280, 1201, 1118, 990, 941, 800 (the peak at 1604 cm$^{-1}$ is a characteristic peak of β-diketone), MS (m/e): 172, 127, 45.

Reference Example 5

Preparation of 2-methoxy-2,6,6-trimethyl-3,5-heptanedione (mmbd)

In a 200 mL-volume flask equipped with a stirrer, a thermometer and a dropping funnel was placed 8.12 g (208 mmol) of sodium amide, and the flask was purged with argon. Then, 80 mL of toluene was placed in the flask. Subsequently, 20.6 g (206 mmol) of 3,3-dimethyl-2-butan-one was slowly dropped into the flask, and the resulting mixture was stirred for 15 minutes. Into the flask was further dropped 14.8 g (112.0 mmol) of methyl 2-methoxy-isobutyrate, and the mixture was stirred for 30 minutes for caring out a reaction. After the reaction was complete, 50 mL of water was placed in the flask under cooling with ice. The aqueous portion was taken out, neutralized with acetic acid, and subjected to extraction with ether. The ether extract was washed with water, dried over anhydrous sodium sulfate, and filtered. The filtrate was concentrated and distilled under reduced pressure (53° C., 200 Pa) to give 10.23 g (yield: 46%) of 2-methoxy-2,6,6-trimethyl-2,4-heptanedione as colorless liquid.

The 2-methoxy-2,6,6-trimethyl-2,4-heptanedione had the following characteristics:

$^1$H-NMR (CDCl$_3$, δ (ppm)): 1.17 (0.72H, s), 1.20 (8.28H, s), 1.29 (0.48H, s), 1.36 (5.52H, s), 3.23 (0.24H, s), 3.24 (2.76H, s), 3.82 (0.16H, s), 6.02 (0.92H, s), 15.8 (0.92H, s), IR (neat, cm$^{-1}$): 2979, 2937, 1603 (br), 1464, 1362, 1181, 1119, 1075, 866, 812 (the peak at 1603 cm$^{-1}$ is a characteristic peak of β-diketone), MS (m/e): 127, 73, 43.

Comparison Example A-1

Preparation of tris(1-methoxy-5,5-dimethyl-2,4-hexanedionato)indium(III)—In(mbd)$_3$ In a 100 mL-volume flask equipped with a stirrer, a thermometer and a dropping funnel was placed 4.48 g (23.2 mmol) of 28% sodium methoxide methanol solution. Into the ice-cooled solution was slowly dropped 4.00 g (23.2 mmol) of 1-methoxy-5,5-dimethyl-2,4-hexanedione (prepared by the method of Reference Example 4), and the mixture was stirred for 5 minutes. Subsequently, a solution of 2.18 g (7.44 mmol) of indium(III) chloride tetrahydrate in 15 mL of methanol was slowly dropped into the mixture. The resulting mixture was stirred under cooling with ice for 30 minutes for carrying out a reaction. After the reaction was complete, the reaction mixture was placed under reduced pressure to distill methanol off. To the residue were added 40 mL of ether and 40 ml of water. The organic portion was taken out, dried over anhydrous sodium sulfate, and filtered. The filtrate was concentrated. The concentrated filtrate was placed under reduced pressure and distilled at 190° C., 15 Pa, to give 3.20 g (yield: 68%) of tris(1-methoxy-5,5-dimethyl-2,4-hexane-dionato)indium(III) as viscous yellow liquid.

The tris(1-methoxy-5,5-dimethyl-2,4-hexanedionato)-indium(III) is a new compound having the following characteristics:

IR (neat, cm$^{-1}$): 2966, 2932, 1566, 1517, 1416, 1383, 1361, 1201, 1163, 1119, 996, 806, 482 (the characteristic peak (1604 cm$^{-1}$) of β-diketone has disappeared, and a characteristic peak (1566 cm$^{-1}$) of β-diketonato appears), Elemental analysis: found: C, 51.3%; H, 7.28%; In, 18%. calculated ($C_{27}H_{45}O_9In$): C, 51.6%; H, 7.22%; In, 18.3%. MS (m/e): 628, 571, 457, 229, 115, 57.

Comparison Example A-2

Preparation of tris(2-methoxy-2,6,6-trimethyl-3,5-heptanedionato)indium(III)—in(mmbd)$_3$ In a 100 mL-volume flask equipped with a stirrer, a thermometer and a dropping funnel was placed 2.98 g (15.5 mmol) of 28% sodium methoxide methanol solution. Into the ice-cooled solution was slowly dropped 3.08 g (15.4 mmol) of 2-methoxy-2,6,6-trimethyl-3,5-heptanedione (prepared by the method of Reference Example 5), and the mixture was stirred for 5 minutes. Subsequently, a solution of 1.53 g (5.22 mmol) of indium(III) chloride tetra-hydrate in 15 mL of methanol was slowly dropped into the mixture. The resulting mixture was stirred under cooling with ice for 30 minutes for carrying out a reaction. After the reaction was complete, the reaction mixture was placed under reduced pressure to distill methanol off. To the residue were added 40 mL of ether and 40 mL of water. The organic portion was taken out, dried over anhydrous sodium sulfate, and filtered. The filtrate was concentrated. The concentrated filtrate was placed under reduced pressure and distilled at 190° C., 37 Pa, to give 2.64 g (yield: 70%) of tris(2-methoxy-2,6,6-trimethyl-3,5-heptanedionato)indium(III) as pale yellow solid.

The tris(2-methoxy-2,6,6-trimethyl-3,5-heptanedionato)indium(III) is a new compound having the following characteristics:

m.p.: 114° C., IR (KBr, cm$^{-1}$): 2980, 2934, 1565, 1502, 1415, 1356, 1230, 1184, 1133, 1075, 953, 866, 816, 734, 619, 535, 484 (the characteristic peak (1603 cm$^{-1}$) of β-diketone has disappeared, and a characteristic peak (1565 cm$^{-1}$) of β-diketonato appears), Elemental analysis: found: C, 55.8%; H, 8.11%; In, 16%. calculated ($C_{33}H_{57}O_9In$): C, 55.6%; H, 8.06%; In, 16.1%. MS (m/e): 682, 513, 449, 313, 241, 115, 73.

Comparison Example A-3

Preparation of bis(1-methoxy-5,5-dimethyl-2,4-hexanedionato)strontium(II)—Sr(mbd)$_2$ In a 100 mL-volume flask equipped with a stirrer, a thermometer and a dropping funnel were placed 0.39 g (4.35 mmol) of strontium(II) hydride and 20 mL of 1,2-dimethoxyethane under an argon atmosphere. Into the ice-cooled mixture was slowly dropped 1.50 g (8.71 mmol) of 1-methoxy-5,5-dimethyl-2,4-hexanedione (prepared by the method of Reference Example 4), and the mixture was stirred at room temperature for one hour for carrying out a reaction. After the reaction was complete, the reaction mixture was concentrated by heating to 230° C. under reduced pressure. To the concentrate was added 15 mL of hexane, and the mixture was filtered. The filtrate was concentrated. A trial for sublime the concentrated filtrate was made at 235° C., 53 Pa. It was merely observed that a black brown solid remained in a sublimation vessel.

Comparison Example A-4

Preparation of bis(2-methoxy-2,6,6-trimethyl-3,5-heptanedionato)strontium(II)—Sr(mmbd)$_2$ In a 100 mL-volume flask equipped with a stirrer, a thermometer and a dropping funnel were placed 0.45 g (5.00 mmol) of strontium(II) hydride and 20 mL of 1,2-dimethoxyethane under an argon atmosphere. Into the ice-cooled mixture was slowly dropped 2.00 g (9.99 mmol) of 2-methoxy-2,6,6-trimethyl-3,5-hexanedione (prepared by the method of Reference Example 5), and the mixture was stirred at room temperature for one hour for carrying out a reaction. After the reaction was complete, the reaction mixture was concentrated by heating to 230° C. under reduced pressure. To the concentrate was added 15 mL of hexane. The resulting mixture was stirred and filtered. The filtrate was concentrated. The concentrated filtrate was sublimed at 235° C., 53 Pa, to give 1.37 g (yield: 56%) of bis(2-methoxy-2,6,6-trimethyl-3,5-heptanedionato)-strontium(II) as pale yellow solid.

The bis(2-methoxy-2,6,6-trimethyl-3,5-heptanedionato)strontium(II) is a new compound having the following characteristics:

m.p.: 235° C., IR (KBr, cm$^{-1}$): 3426, 2970, 2867, 1607, 1500, 1461, 1426, 1386, 1361, 1226, 1178, 1121; 1078, 1052, 966, 858, 789, 723, 478,

Elemental analysis: found: C, 54.3%; H, 7.81%; Sr, 18%. calculated ($C_{22}H_{38}O_6Sr$): C, 54.4%; H, 7.88%; Sr, 18.0%. MS (m/e): 1259, 773, 73.

From the MS data, the strontium complex compound is considered to have a trimer structure.

Example A-13

Comparison of Thermal Stability and Melting Point of Indium Complex Compound

In a 25 mL-volume flask was placed 0.50 g of the indium complex compound prepared in Example A-1, Comparison Example A-1, or Comparison Example A-2. The indium complex compound was heated to 190° C. for 15 minutes under an argon atmosphere, and its appearance was observed. The results are set forth in Table 1.

TABLE 1

| Metal complex compound | Results of thermal stability test-appearance |
|---|---|
| Ex. 1 In(mopd)$_3$ | No change-pale yellow remained pale yellow liquid |
| Com. 1 In(mbd)$_3$ | Turned to black brown pale yellow liquid |
| Com. 2 In(mmbd)$_3$ | No change-pale yellow remained pale yellow solid (m.p.: 114° C.) |

TABLE 1-continued

| Metal complex compound | Results of thermal stability test-appearance |
|---|---|

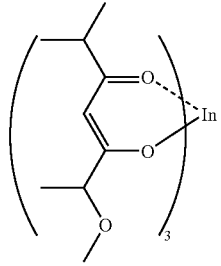

In(mopd)₃      In(mbd)₃

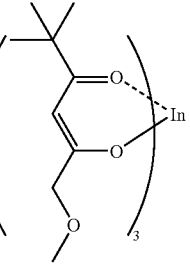

In(mmbd)₃

The results in Table 1 indicate that In(mbd)₃ of Comparison Example 1 has a low melting point but shows poor thermal stability and that In(mmbd)₃ of Comparison Example 2 shows good thermal stability but has a high melting point. In contrast, In(mopd)₃ of Example 1 shows good thermal stability and has a low melting point.

Example A-14

Comparison of Thermal Stability and Melting Point of Strontium Complex Compound

In a 25 mL-volume flask was placed 0.30 g of the strontium complex co-pound prepared in Example A-4, Comparison Example A-3, or Comparison Example A-4. The strontium complex compound was heated to 235° C. for 15 minutes under reduced pressure (40 Pa), and its appearance was observed. The results are set forth in Table 2.

TABLE 2

| Metal complex compound | Results of thermal stability test-appearance |
|---|---|
| Ex. 4 Sr(mopd)₃ | No change-130° C. |
| Com. 3 Sr(mbd)₃ | Turned to black brown-110° C. |
| Com. 4 Sr(mmbd)₃ | No change-235° C. |

TABLE 2-continued

| Metal complex compound | Results of thermal stability test-appearance |
|---|---|

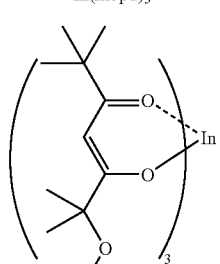

Sr(mobd)₃      Sr(mbd)₃

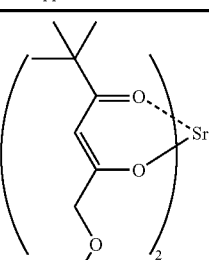

Sr(mmbd)₃

The results in Table 2 indicate that Sr(mbd) 3 of Comparison Example 3 has a low melting point but shows poor thermal stability and that Sr(mmbd)₃ of Comparison Example 4 shows good thermal stability but has a high melting point. In contrast, Sr(mopd)₃ of Example 4 shows good thermal stability and has a low melting point.

Examples A-15 to A-24

Deposition Tests

Preparation of Metal Oxide Film

The deposition experiment by the CVD method was performed using a metal complex compound prepared in Examples A-1 and A-4 to A-12 (indium complex compound (In(mopd)₃), strontium complex compound (Sr(mobd)₂) zinc complex compound (Zn(mopd)₂), tin complex compound (Sn(mopd)₂), vanadium complex compound (V(mopd)₃), aluminum complex compound (Al(mopd)₃), magnesium complex compound (Mg(mopd)₂), lead complex compound (Pb(mopd)₂) barium complex compound (Ba(mobd)₂), or gallium complex compound (Ga(mopd)₃), to evaluate the film-forming property.

The experiment for evaluation was performed using an apparatus illustrated in FIG. 1. The metal complex compound 20 placed in a vaporizer (glass ampul) 3 is heated by a heater 10B to vaporize. The vapor passes through a mass flow controller 1A and comes out of the vaporizer 3 together with a helium gas which is supplied after heating in a pre-heater 10A. The vapor having come out of the vaporizer 3 enters a reactor 4 together with an oxygen gas which is supplied through a mass flow controller 1B and a stop valve 2. The pressure in the reactor is regulated to a predetermined value by on-off of a valve 6 arranged in a position prior to the vacuum pump and monitored by means of a pressure gauge 5.

The center portion of the glass reactor is so constituted that it can be heated by a heater 10C. The metal complex compound supplied into the reactor oxidatively decomposes on a surface of a substrate 21 for receiving deposition which is arranged in the reactor at the central position and heated to a predetermined temperature by the heater 10C, so that a metal oxide film deposits on the substrate 21. The gas coming out of the reactor 4 is exhausted into the atmosphere through a trap 7 and a vacuum pump.

The deposition conditions are set forth below:
Flow rate of He carrier: 30 mL/min.
Flow rate of oxygen: 20 mL/min.
Substrate: $SiO_2$/Si (size: 7 mm×40 mm)
Temperature of substrate: 400° C.
Pressure in reactor: 5,320 Pa
Deposition period: 30 minutes The results of deposition (film property and analysis of product were performed by XPS analysis) are set forth in Table 3.

TABLE 3

| | Metal complex compound | Vaporizing temperature | Film property (film thickness) |
|---|---|---|---|
| Ex. A-15 | In(mopd)$_3$ | 140° C. | Indium oxide (40 nm) |
| Ex. A-16 | Sr(mobd)$_2$ | 220° C. | Strontium oxide (30 nm) |
| Ex. A-17 | Zn(mopd)$_2$ | 220° C. | Zinc oxide (50 nm) |
| Ex. A-18 | Sn(mopd)$_2$ | 140° C. | Tin oxide (45 nm) |
| Ex. A-19 | V(mopd)$_3$ | 160° C. | Vanadium oxide (40 nm) |
| Ex. A-20 | Al(mopd)$_3$ | 140° C. | Aluminum oxide (35 nm) |
| Ex. A-21 | Mg(mopd)$_2$ | 190° C. | Magnesium oxide (40 nm) |
| Ex. A-22 | Pb(mopd)$_2$ | 160° C. | Lead oxide (35 nm) |
| Ex. A-23 | Ba(mopd)$_2$ | 230° C. | Barium oxide (30 nm) |
| Ex. A-24 | Ga(mopd)$_3$ | 140° C. | Gallium oxide (35 nm) |

The results shown in Table 3 indicate that the metal complex compounds of the invention have a good film-forming property.

Reference Example 6

Preparation of 2-methoxy-3,5-octanedione—mood

In a 200 mL-volume flask equipped with a stirrer, a thermometer and a dropping funnel was placed 10.1 g (259 mmol) of sodium amide, and the flask was purged with argon. Then, 100 mL of toluene was placed in the flask. Subsequently, 14.4 g (167 mmol) of 2-pentanone was slowly dropped into the flask, and the resulting mixture was stirred for 15 minutes. Into the flask was further dropped 15.0 g (127 mmol) of methyl 2-methoxypropionate (prepared by the method of Reference Example 1), and the mixture was stirred for one hour for carrying out a reaction After the reaction was complete, 50 mL of water was placed in the flask under cooling with ice. The aqueous portion was taken out, made acidic by 2.5 mol/L sulfuric acid, and subjected to extraction with hexane. The hexane extract was washed with water, dried over anhydrous sodium sulfate, and filtered. The filtrate was concentrated and distilled under reduced pressure (35° C., 20 Pa) to give 14.3 g (yield: 65%) of 2-methoxy-3,5-octanedione as colorless liquid.

The 2-methoxy-3,5-octanedione had the following characteristics:

$^1$H-NMR (CDCl$_3$, δ (ppm)): 0.94-0.99 (3H, m), 1.35 (3H, d), 1.6-1.7 (2H, m), 2.29-2.34 (1.7H, m), 2.51 (0.3H, m), 3.36 (3H, s), 3.60 (0.3H, s), 3.74 (1H, q), 5.79 (0.85H, s), 15.3 (0.85H, s), IR (neat, cm$^{-1}$): 2967, 2936, 2977, 2827, 1608 (br), 1458, 1332, 1210, 1119, 802 (the peak at 1608 cm$^{-1}$ is a characteristic peak of β-diketone), MS (m/e): 142, 113, 59, 28.

Example A-25

Preparation of tris(2-methoxy-3,5-octane-dionato) indium(III)—In(mood)$_3$

In a 100 mL-volume flask equipped with a stirrer, a thermometer and a dropping funnel was placed 5.71 g (29.6 mmol) of 28% sodium methoxide methanol solution. Into the ice-cooled solution was slowly dropped 5.18 g (30.0 mmol) of 2-methoxy-3,5-octanedione (prepared by the method of Reference Example 6), and the mixture was stirred for 5 minutes. Subsequently, a solution of 2.85 g (9.72 mmol) of indium(III) chloride tetrahydrate in 10 mL of methanol was slowly added to the mixture. The resulting mixture was stirred for one hour under cooling with ice for carrying out a reaction. After the reaction was complete, the reaction mixture was placed under reduced pressure to distill methanol off. To the residue were added 30 mL of hexane and 30 mL of water. The organic portion was taken out, dried over anhydrous sodium sulfate, and filtered. The filtrate was concentrated. The concentrated filtrate was placed under reduced pressure and distilled at 185° C., 19 Pa, to give 4.01 g (yield: 66%) of tris(2-methoxy-3,5-octanedionato)indium(III) as viscous yellow liquid.

The tris(2-methoxy-3,5-octanedionato)indium(III) is a new compound having the following characteristics:

IR (neat, cm$^{-1}$): 2964, 2933, 2875, 2824, 1572, 1521, 1427, 1397, 1211, 1120, 957, 808, 543 (the characteristic peak (1608 cm$^{-1}$) of β-diketone has disappeared, and a characteristic peak (1572 cm$^{-1}$) of β-diketonato appears), Elemental analysis: found: C, 51.5%; H, 7.24%; In, 18.2%. calculated (C$_{27}$H$_{45}$O$_9$In): C, 51.6%; H, 7.22%; In, 18.3%. MS (m/e): 628, 598, 457, 227, 113, 59.

Example A-26

Preparation of bis(2-methoxy-3,5-octane-dionato) zinc(II)—Zn(mood)$_2$

In a 100 mL-volume flask equipped with a stirrer, a thermometer and a dropping funnel were placed 4.62 g (24.0 mmol) of 28% sodium methoxide methanol solution and 6 mL of methanol. Into the ice-cooled solution was slowly dropped 4.11 g (23.9 mmol) of 2-methoxy-3,5-octane-dione (prepared by the method of Reference Example 6), and the mixture was stirred for 5 minutes. Subsequently, a solution of 1.60 g (11.7 mmol) of zinc (II) chloride in 4 mL of methanol was slowly dropped into the mixture. The resulting mixture was stirred for one hour at room temperature for carrying out a reaction. After the reaction was complete, the reaction mixture was placed under reduced pressure to distill methanol off. To the residue were added 30 mL of hexane and 30 mL of water. The organic portion was taken out, dried over anhydrous sodium sulfate, and filtered. The filtrate was concentrated. The concentrated filtrate was placed under reduced pressure and distilled at 160° C., 17 Pa, to give 4.02 g (yield: 84%) of bis(2-methoxy-3,5-octanedionato)zinc(II) as yellow liquid.

The bis(2-methoxy-3,5-octanedionato) zinc(II) is a new compound having the following characteristics:

IR (neat, cm$^{-1}$): 2963, 2933, 2874, 2823, 1598, 1522, 1431, 1334, 1211, 1119, 959, 796, 537 (the characteristic peak (1608 cm$^{-1}$) of β-diketone has disappeared, and a characteristic peak (1598 cm$^{-1}$) of β-diketonato appears), Elemental analysis: found: C, 53.1%; H, 7.45%; Zn, 16%. calculated ($C_{18}H_{30}O_6Zn$): C, 53.0%; H, 7.41%; Zn, 16.0%. MS (m/e): 406, 347, 113, 59.

Example A-27

Preparation of bis(2-methoxy-3,5-octane-dionato)tin (II)—Sn(mood)$_2$

In a 100 mL-volume flask equipped with a stirrer, a thermometer and a dropping funnel were placed 4.64 g (24.1 mmol) of 28% sodium methoxide methanol solution and 6 mL of methanol. Into the ice-cooled solution was slowly dropped 4.21 g (24.4 mmol) of 2-methoxy-3,5-octane-dione (prepared by the method of Reference Example 6), and the mixture was stirred for 5 minutes. Subsequently, a solution of 2.23 g (11.8 mmol) of tin(II) chloride in 6 mL of methanol was slowly dropped into the mixture. The resulting mixture was stirred for one hour at room temperature for carrying out a reaction. After the reaction was complete, the reaction mixture was placed under reduced pressure to distill methanol off. To the residue was added 30 mL of hexane. The organic portion was taken out, dried over anhydrous sodium sulfate, and filtered. The filtrate was concentrated. The concentrated filtrate was placed under reduced pressure and distilled at 160° C., 16 Pa, to give 3.40 g (yield: 63%) of bis(2-methoxy-3,5-octanedionato)tin(II) as pale yellow liquid.

The bis(2-methoxy-3,5-octanedionato)tin(II) is a new compound having the following characteristics:

IR (neat, cm$^{-1}$): 2974, 2932, 2873, 2823, 1573, 1511, 1411, 1327, 1210, 1119, 953, 912, 808, 545 (the characteristic peak (1608 cm$^{-1}$) of β-diketone has disappeared, and a characteristic peak (1573 cm$^{-1}$) of β-diketonato appears).

Elemental analysis: found: C, 46.8%; H, 6.59%; Sn, 25.6%. calculated ($C_{18}H_{30}O_6Sn$): C, 46.9%; H, 6.56%; Sn, 25.7%. MS (m/e): 403, 291, 113, 59.

Example A-28

Preparation of tris(2-methoxy-3,5-octane-dionato) aluminum(III)—Al(mood)$_3$

In a 100 mL-volume flask equipped with a stirrer, a thermometer and a dropping funnel were placed 4.56 g (23.6 mmol) of 28% sodium methoxide methanol solution and 6 mL of methanol. Into the ice-cooled mixture was slowly dropped 4.15 g (24.1 mmol) of 2-methoxy-3,5-octanedione (prepared by the method of Reference Example 6). The resulting mixture was stirred for 5 minutes. To the mixture was added a solution of 1.03 g (7.72 mmol) of aluminum (III) chloride in 10 mL of methanol, and the resulting mixture was stirred at room temperature for carrying out a reaction. After the reaction was complete, the reaction mixture was placed under reduced pressure to distill methanol off. To the residue were added 30 mL of hexane and 30 mL of water. The organic portion was taken out, dried over anhydrous sodium sulfate, and filtered. The filtrate was concentrated. The concentrated filtrate was placed under reduced pressure and distilled at 180° C., 13 Pa, to give 1.90 g (yield: 46%) of tris(2-methoxy-3,5-octanedionato)aluminum(III) as colorless liquid.

The tris(2-methoxy-3,5-octanedionato)aluminum (III) is a new compound having the following characteristics:

IR (neat, cm$^{-1}$): 2963, 2933, 2874, 2824, 1585, 1528, 1458, 1414, 1330, 1212, 1121, 977, 796, 552 (the characteristic peak (1608 cm$^{-1}$) of β-diketone has disappeared, and a characteristic peak (1585 cm$^{-1}$) of β-diketonato appears), Elemental analysis: found: C, 59.9%; H, 8.37%; Al, 5.0%. calculated ($C_{27}H_{45}O_9Al$): C, 60.0%; H, 8.39%; Al, 4.99%. MS (m/e): 540, 510, 481, 369, 113, 59.

Example A-29

Preparation of bis(2-methoxy-3,5-octane-dionato) lead(II)—Pb(Mood)$_2$

In a 100 mL-volume flask equipped with a stirrer, a thermometer and a dropping funnel were placed 4.52 g (23.4 mmol) of a sodium methoxide methanol solution and 6 mL of methanol. Into the ice-cooled mixture was slowly dropped 4.20 g (24.4 mmol) of 2-methoxy-3,5-octanedione (prepared by the method of Reference Example 6). The resulting mixture was stirred for 5 minutes. To the mixture was added 3.12 g (11.2 mmol) of lead(II) chloride, and the resulting mixture was stirred at room temperature for carrying out a reaction. After the reaction was complete, the reaction mixture was placed under reduced pressure to distill methanol off. To the residue were added 30 mL of hexane and 30 mL of water. The organic portion was taken out, dried over anhydrous sodium sulfate, and filtered. The filtrate was concentrated. The concentrated filtrate was placed under reduced pressure and distilled at 205° C., 51 Pa, to give 4.66 g (yield: 76%) of bis(2-methoxy-3,5-octanedionato)lead(II) as viscous orange liquid.

The bis(2-methoxy-3,5-octanedionato)lead(II) is a new compound having the following characteristics:

IR (neat, cm$^{-1}$): 2962, 2932, 2873, 2822, 1590, 1515, 1419, 1333, 1211, 1117, 1016, 953, 788 (the characteristic peak (1608 cm$^{-1}$) of β-diketone has disappeared, and a characteristic peak (1590 m$^{-1}$) of β-diketonato appears), Elemental analysis: found: C, 39.2%; H, 5.53%; Pb, 37.5%. calculated ($C_{18}H_{30}O_6Pb$): C, 39.3%; H, 5.50%; Pb, 37.7%. MS (m/e): 550, 398, 339, 249, 113, 59.

Example A-30

Preparation of bis(2-methoxy-3,5-octane-dionato) magnesium(II)—Mg(mood)$_2$

In a 100 mL-volume flask equipped with a stirrer, a thermometer and a dropping funnel were placed 0.66 g (11.3 mmol) of magnesium(II) hydroxide and 20 mL of 1,2-dimethoxyethane. Subsequently, 4.13 g (24.0 mmol) of 2-methoxy-3,5-octanedione (prepared by the method of Reference Example 6) were slowly dropped. The resulting mixture was stirred at room temperature for one hour for carrying out a reaction. After the reaction was complete, the reaction mixture was concentrated under reduced pressure. The concentrate was then distilled under reduced pressure at 230° C., 32 Pa, to give 3.31 g (yield: 80%) of bis(2-methoxy-3,5-octanedionato)magnesium(II) as viscous yellow liquid.

The bis(2-methoxy-3,5-octanedionato)magnesium(II) is a new compound having the following characteristics:

IR (neat, cm$^{-1}$): 2962, 2932, 2873, 2822, 1610, 1521, 1436, 1336, 1212, 1117, 964, 792, 532, Elemental analysis: found: C, 58.9%; H, 8.28%; Mg, 6.6%. calculated ($C_{18}H_{30}O_6Mg$): C, 59.0%; H, 8.25%; Mg, 6.63%. MS (m/e): 561, 307, 59.

From the MS data, the magnesium complex compound is considered to have a dimer structure.

Example A-31

Preparation of tris(2-methoxy-3,5-octane-dionato)gallium(III)—Ga(mood)$_3$

In a 100 mL-volume flask equipped with a stirrer, a thermometer and a dropping funnel was placed 5.08 g (26.3 mmol) of 28% sodium methoxide methanol solution and 10 mO of methanol. Into the ice-cooled solution was slowly dropped 4.56 g (26.5 mmol) of 2-methoxy-3,5-octanedione (prepared by the method of Reference Example 6), and the mixture was stirred for 5 minutes. Subsequently, 1.52 g (8.63 mmol) of gallium(III) chloride was slowly dropped into the mixture. The resulting mixture was stirred at room temperature for one hour for carrying out a reaction. After the reaction was complete, the reaction mixture was placed under reduced pressure to distill methanol off. To the residue were added 30 mL of hexane and 30 mL of water. The organic portion was taken out, dried over anhydrous sodium sulfate, and filtered. The filtrate was concentrated. The concentrated filtrate was placed under reduced pressure and distilled at 175° C., 17 Pa, to give 4.07 g (yield: 81%) of tris(2-methoxy-3,5-octanedionato)gallium(III) as pale yellow liquid.

The tris(2-methoxy-3,5-octanedionato)gallium(III) is a new compound having the following characteristics:

IR (neat, cm$^{-1}$): 2963, 2933, 2874, 2823, 1576, 1528, 1435, 1403, 1330, 1211, 1120, 966, 801, 550 (the characteristic peak (1608 cm$^{-1}$) of β-diketone has disappeared, and a characteristic peak (1576 cm$^{-1}$) of β-diketonato appears Elemental analysis: found: C, 55.7%; H, 7.75%; Ga, 12%. calculated ($C_{27}H_{45}O_9Ga$): C, 55.6%; H, 7.78%; Ga, 12.0%. MS (m/e): 582, 523, 411, 59.

Examples A-32 to A-38

Deposition Tests

Preparation of Metal Oxide Film

The deposition experiment by the CVD method according to the aforementioned procedures was performed using a metal complex compound prepared in Examples A-25 to A-31 (indium complex compound (In(mood)$_3$), zinc complex compound (Zn(mood)$_2$), tin complex compound (Sn(mood)2), aluminum complex compound (Al(mood)$_3$), lead complex compound (Pb(mood) 2) magnesium complex compound (Mg(mood)$_2$), or gallium complex compound (Ga(mood)$_3$), to evaluate the film-forming property.

The deposition conditions are set forth below:
Flow rate of He carrier: 30 mL/min.
Flow rate of oxygen: 20 mL/min.
Substrate: SiO$_2$/Si (size: 7 mm×40 mm)
Temperature of substrate: 400° C.
Pressure in reactor: 7,980 Pa
Deposition period: 60 minutes The results of deposition (film property and analysis of product were performed by XPS analysis) are set forth in Table 4.

TABLE 4

| | Metal complex compound | Vaporizing temperature | Film property (film thickness) |
|---|---|---|---|
| Ex. A-32 | In(mood)$_3$ | 140° C. | Indium oxide (40 nm) |
| Ex. A-33 | Zn(mood)$_2$ | 100° C. | Zinc oxide (35 nm) |
| Ex. A-34 | Sn(mood)$_2$ | 120° C. | Tin oxide (35 nm) |
| Ex. A-35 | Al(mood)$_3$ | 140° C. | Aluminum oxide (40 nm) |
| Ex. A-36 | Pb(mood)$_2$ | 130° C. | Lead oxide (30 nm) |
| Ex. A-37 | Mg(mood)$_2$ | 170° C. | Barium oxide (40 nm) |
| Ex. A-38 | Ga(mood)$_3$ | 140° C. | Gallium oxide (45 nm) |

The results shown in Table 4 indicate that the metal complex compounds of the invention have a good film-forming property.

Reference Example 7

Preparation of 2-methoxy-3,5-hexanedione (momd)

In a 200 mL-volume flask equipped with a stirrer, a thermometer and a dropping funnel was placed 10.1 g (259 mmol) of sodium amide, and the flask was purged with argon. Then, 120 mL of methylcyclohexane was placed in the flask. Subsequently, 7.40 g (127 mmol) of acetone was slowly dropped into the ice-cooled mixture in the flask, and the resulting mixture was stirred for 15 minutes. Into the flask was further dropped 15.0 g (127 mmol) of methyl 2-methoxypropionate (prepared by the method of Reference Example 1), and the mixture was stirred for 30 minutes for carrying out a reaction. After the reaction was complete, 50 mL of water was placed in the flask under cooling with ice. The aqueous portion was taken out, made acetic with acetic acid, and subjected to extraction with hexane. The hexane extract was washed with water, dried over anhydrous sodium sulfate, and filtered. The filtrate was concentrated and distilled under reduced pressure (66° C., 1.38 kPa) to give 9.63 g (yield: 53%) of 2-methoxy-3,5-hexanedione as colorless liquid.

The 2-methoxy-3,5-hexanedione had the following characteristics:

$^1$H-NMR (CDCl$_3$, δ (ppm)): 1.30 (0.33H, d), 1.35 (2.67H, d), 2.11 (2.67H, s), 2.26 (0.22H, s), 3.36 (2.67H, s), 3.37 (0.33H, s), 3.70-3.81 (1.22H, m), 5.80 (0.89H, s), 15.27 (0.89H, s), IR (neat, cm$^{-1}$): 2987, 2937, 2828, 1611 (br), 1451, 1368, 1211, 1119, 801 (the peak at 1611 cm$^{-1}$ is a characteristic peak of β-diketone), MS (m/e): 114, 85, 59, 43, 27.

Reference Example 8

Preparation of 2-methoxy-3,5-heptanedione (mohd)

In a 200 mL-volume flask equipped with a stirrer, a thermometer and a dropping funnel was placed 8.00 g (205 mmol) of sodium amide, and the flask was purged with argon. Then, 50 mL of toluene was placed in the flask. Subsequently, 15.0 g (208 mmol) of 2-butanone was slowly dropped into the ice-cooled mixture in the flask, and the resulting mixture was stirred for 10 minutes. The mixture was cooled to 5° C., and Into the cooled mixture was further dropped 8.50 g (72 mmol) of methyl 2-methoxypropionate (prepared by the method of Reference Example 1), and the mixture was stirred for 30 minutes for carrying out a reaction. After the reaction was complete, 40 mL of water was placed in the flask under cooling with ice. The aqueous portion was taken out, made acetic with 2.5 mol/L sulfuric acid, and subjected to extraction with diethyl ether. The diethyl ether extract was washed with water, dried over anhydrous sodium sulfate, and filtered. The filtrate was concentrated and distilled under reduced pressure (32° C., 26.6 Pa) to give 5.60 g (yield: 49%) of 2-methoxy-3,5-heptanedione as colorless liquid.

The 2-methoxy-3,5-heptanedione had the following characteristics:

$^1$H-NMR (CDCl$_3$, δ (ppm)): 1.08 (0.48H, t), 1.16 (2.52H, t), 1.30 (0.48H, d), 1.36 (2.52H, d), 2.38 (1.68H, q), 2.56 (0.32H, q), 3.37 (3H, s), 3.45 (0.32H, s), 3.71-2.81 (1H, m), 5.80 (0.84H, s), 15.3 (0.84H, s), IR (neat, cm$^{-1}$): 2984, 2939, 2828, 1610 (br), 1458, 1328, 1210, 1119, 1063, 882, 814 (the peak at 1610 cm$^{-1}$ is a characteristic peak of β-diketone), MS (m/e): 128, 99, 59, 43, 29.

Example B-1

Preparation of tris(2-methoxy-6-methyl-3,5-heptanedionato)chromium(III)—Cr(mopd) 3)

In a 100 mL-volume flask equipped with a stirrer, a thermometer and a dropping funnel was placed 4.58 g (23.7 mmol) of 28% sodium methoxide methanol solution. Into the ice-cooled solution was slowly dropped 4.26 g (22.1 mmol) of 2-methoxy-6-methyl-3,5-heptanedione (prepared by the method of Reference Example 2), and the mixture was stirred for 5-minutes. Subsequently, a solution of 2.01 g (7.54 mmol) of chromium(III) chloride hexahydrate in 10 mL of methanol was slowly dropped to the mixture. The resulting mixture was stirred for 30 minutes under cooling with ice for carrying out a reaction. After the reaction was complete, the reaction mixture was placed under reduced pressure to distill methanol off. To the residue were added 15 mL of mesitylene. The resulting mixture was then refluxed for one hour, and cooled to room temperature. To the mixture was added 40 ml of water. The organic portion was taken out, dried over anhydrous sodium sulfate, and filtered. The filtrate was concentrated. The concentrated filtrate was placed under reduced pressure and distilled at 180° C., 23 Pa, to give 2.54 g (yield: 60%) of tris(2-methoxy-6-methyl-3,5-heptanedionato)chromium(III) as viscous red-violet liquid.

The tris(2-methoxy-6-methyl-3,5-heptanedionato)-chromium(III) is a new compound having the following characteristics:

IR (neat, cm$^{-1}$): 2975, 2933, 1568, 1530, 1415, 1333, 1239, 1120, 914, 800, 571 (the characteristic peak (1607 cm$^{-1}$) of β-diketone has disappeared, and a characteristic peak (1568 cm$^{-1}$) of β-diketonato appears), Elemental analysis: found: C, 57.2%; H, 8.05%; Cr, 9.2%. calculated (C$_{27}$H$_{45}$O$_9$Cr): C, 57.3%; H, 8.02%; Cr, 9.19%. MS (m/e): 565, 535, 394, 59.

Example B-2

Preparation of bis(2-methoxy-6-methyl-3,5-heptanedionato)Manganese(II)—Mn(mopd)$_2$ In a 100 mL-volume flask equipped with a stirrer, a thermometer and a dropping funnel was placed 2.71 g (14.1 mmol) of 28% sodium methoxide methanol solution. Into the ice-cooled solution was slowly dropped 3.30 g (10.2 mmol) of 2-methoxy-6-methyl-3,5-heptanedione (prepared by the method of Reference Example 2), and the mixture was stirred for 5 minutes. Subsequently, a solution of 1.18 g (5.96 mmol) of manganese(II) chloride tetrahydrate in 6 mL of methanol was slowly dropped into the mixture. The resulting mixture was stirred for one hour under cooling with ice for carrying out a reaction. After the reaction was complete, the reaction mixture was placed under reduced pressure to distill methanol off. To the residue were added 30 mL of hexane and 30 mL of water. The organic portion was taken out, dried over anhydrous sodium sulfate, and filtered. The filtrate was concentrated. The concentrated filtrate was placed under reduced pressure and distilled at 220° C., 23 Pa, to give 1.60 g (yield: 47%) of bis(2-methoxy-6-methyl-3,5-heptanedionato)-manganese(II) as viscous brown liquid.

The bis(2-methoxy-6-methyl-3,5-heptanedionato)-manganese(II) is a new compound having the following characteristics:

IR (neat, cm$^{-1}$): 3375 (br), 2971, 2932, 1601, 1510, 1431, 1332, 1211, 1150, 1118, 1020, 955, 911, 804, 546, Elemental analysis: found: C, 54.7%; H, 7.65%; Mn, 13.7%. calculated (C$_{10}$H$_{30}$O$_6$Mn): C, 54.4%; H, 7.61%; Mn, 13.8%. MS (m/e): 623, 397, 338, 168, 59.

From the MS data, the manganese complex compound is considered to have a dimer structure.

Example B-3

Preparation of bis(2-methoxy-6-methyl-3,5-heptanedionato)nickel(II)—Ni(mopd)$_2$ In a 100 mL-volume flask equipped with a stirrer, a thermometer and a dropping funnel was placed 4.53 g (23.5 mmol) of 28% sodium methoxide methanol solution. Into the ice-cooled solution was slowly dropped 4.13 g (24.0 mmol) of 2-methoxy-6-methyl-3,5-heptanedione (prepared by the method of Reference Example 2), and the mixture was stirred for 5 minutes. Subsequently, a solution of 2.78 g (11.7 mmol) of nickel(II) chloride hexahydrate in 6 mL of methanol was slowly dropped into the mixture. The resulting mixture was stirred for one hour under cooling with ice for carrying out a reaction. After the reaction was complete, the reaction mixture was placed under reduced pressure to distill methanol off. To the residue were added 30 mL of hexane and 30 mL of water. The organic portion was taken out, dried over anhydrous sodium sulfate, and filtered. The filtrate was concentrated. The concentrated filtrate was placed under reduced pressure and distilled at 200° C., 25 Pa, to give 4.25 g (yield: 91%) of bis(2-methoxy-6-methyl-3,5-heptanedionato)-nickel(II) as viscous green glassy solid.

The bis(2-methoxy-6-methyl-3,5-heptanedionato)-nickel (II) is a new compound having the following characteristics:

m.p.: 46° C., IR (KBr, cm$^{-1}$): 3410 (br), 2972, 2932, 1599, 1510, 1430, 1333, 1211, 1153, 1117, 912, 806, 566,

Elemental analysis: found: C, 53.8%; H, 7.57%; Ni, 14.5%. calculated (C$_{18}$H$_{30}$O$_6$Ni): C, 53.9%; H, 7.54%; Ni, 14.6%. MS (m/e): 629, 400, 357, 59.

From the MS data, the nickel complex compound is considered to have a dimer structure.

Example B-4

Preparation of bis(2-methoxy-6-methyl-3,5-heptanedionato)cobalt(II)—Co(mopd)$_2$ In a 100 mL-volume flask equipped with a stirrer, a thermometer and a dropping funnel was placed 4.37 g (22.7 mmol) of 28% sodium methoxide methanol solution. Into the ice-cooled solution was slowly dropped 4.00 g (23.2 mmol) of 2-methoxy-6-methyl-3,5-heptanedione (prepared by the method of Reference Example 2), and the mixture was stirred for 5 minutes. Subsequently, a solution of 2.70 g (11.3 mmol) of cobalt(II) chloride hexahydrate in 20 mL of methanol was slowly dropped into the mixture. The resulting mixture was stirred for 30 minutes under cooling with ice for carrying out a reaction. After the reaction was complete, the reaction mixture was placed under reduced pressure to distill methanol off. To the residue were added 50 mL of ether and 30 mL of water. The organic portion was taken out, dried over anhydrous sodium sulfate, and filtered. The filtrate was concentrated. The concentrated filtrate was placed under reduced pressure and distilled at 175° C., 67 Pa, to give 4.17 g (yield: 92%) of bis(2-methoxy-6-methyl-3,5-heptane-dionato)cobalt(II) as viscous dark violet liquid.

The bis(2-methoxy-6-methyl-3,5-heptanedionato)-cobalt (II) is a new compound having the following characteristics:

IR (neat, cm$^{-1}$): 3397 (br), 2972, 2932, 1599, 1511, 1431, 1333, 1211, 1117, 1059, 912, 803, 563 (the characteristic peak (1607 cm$^{-1}$) of β-diketone has disappeared, and a characteristic peak (1599 cm$^{-1}$) of β-diketonato appears), Elemental analysis: found: C, 53.8%; H, 7.56%; Co, 14.6%. calculated ($C_{18}H_{30}O_6Co$): C, 53.9%; H, 7.53%; Co, 14.7%. MS (m/e): 631, 401, 358, 59.

From the MS data, the cobalt complex compound is considered to have a dimer structure.

Example B-5

Preparation of tetrakis(2-methoxy-6-methyl-3,5-heptanedionato)titanium(IV)—Ti(mopd)$_4$ In a 100 mL-volume flask equipped with a stirrer, a thermometer and a dropping tunnel were placed 1.31 g (5.73 mmol) of titanium(IV) tetraethoxide and 4.00 g (23.2 mmol) of 2-methoxy-6-methyl-3,5-heptanedione (prepared by the method of Reference Example 2). The mixture was stirred at 140° C. for one hour for carrying out a reaction with distillation-off of ethanol. After the reaction was complete, 20 mL of hexane and 20 mL of water were added. The organic portion was taken out, dried over anhydrous sodium sulfate, and filtered. The filtrate was concentrated. The concentrated filtrate was placed under reduced pressure and distilled at 180° C., 27 Pa, to give 1.65 g (yield: 39%) of tetrakis(2-methoxy-6-methyl-3,5-heptanedionato)titanium(IV) as dark violet liquid.

The tetrakis(2-methoxy-6-methyl-3,5-heptanedionato)-titanium(VI) is a new compound having the following characteristics:

IR (neat, cm$^{-1}$): 2973, 2932, 1577, 1531, 1408, 1328, 1231, 1119, 1065, 915, 803, 601 (the characteristic peak (1607 cm$^{-1}$) of β-diketone has disappeared, and a characteristic peak (1577 cm$^{-1}$) of β-diketonato appears), Elemental analysis; found: C, 59.1%; H, 8.28%; Ti, 6.5%. calculated ($C_{36}H_{60}O_{12}Ti$): C, 59.0%; H, 8.25%; Ti, 6.53%. MS (m/e): 561, 435, 309, 59.

Example B-6

Preparation of tetrakis(2-methoxy-3,5-octanedionato)zirconium(IV)—Zr(mood)$_4$

In a 100 mL-volume flask equipped with a stirrer, a thermometer and a dropping funnel was placed 4.72 g (24.5 mmol) of 28% sodium methoxide methanol solution. Into the ice-cooled solution was slowly dropped 4.15 g (24.1 mmol) of 2-methoxy-3,5-octanedione (prepared by the method of Reference Example 6), and the mixture was stirred for 5 minutes. Subsequently, a solution of 1.39 g (5.96 mmol) of zirconium(IV) chloride in 6 mL of methanol was slowly dropped into the mixture. The resulting mixture was stirred at room temperature for one hour for carrying out a reaction. After the reaction was complete, the reaction mixture was placed under reduced pressure to distill methanol off. To the residue were added 30 mL of hexane and 30 mL of water. The organic portion was taken out, dried over anhydrous sodium sulfate, and filtered. The filtrate was concentrated. The concentrated filtrate was placed under reduced pressure and distilled at 220° C., 41 Pa, to give 3.47 g (yield: 75%) of tetrakis (2-methoxy-3,5-octanedionato)zirconium(IV) as viscous yellow liquid.

The tetrakis(2-methoxy-3,5-octanedionato)zirconium (VI) is a new compound having the following characteristics:

IR (neat, cm$^{-1}$): 2962, 2932, 2873, 2822, 1595, 1526, 1417, 1329, 1211, 1120, 975, 794, 574, 520 (the characteristic peak (1608 cm$^{-1}$) of β-diketone has disappeared, and a characteristic peak (1595 cm$^{-1}$) of β-diketonato appears, Elemental analysis: found: C, 55.8%; H, 7.76%; Zr, 11.7%. calculated ($C_{36}H_{60}O_{12}Zr$): C, 55.7%; H, 7.79%; Zr, 11.8%. MS (m/e): 603, 113, 59.

Example B-7

Preparation of tetrakis(2-methoxy-3,5-octanedionato)hafnium(IV)—Hf(mood)$_4$

In a 100 mL-volume flask equipped with a stirrer, a thermometer and a dropping funnel was placed 4.88 g (25.3 mmol) of 28% sodium methoxide methanol solution. Into the ice-cooled solution was slowly dropped 4.41 g (25.6 mmol) of 2-methoxy-3,5-octanedione (prepared by the method of Reference Example 6), and the mixture was stirred for 5 minutes. Subsequently, a solution of 2.00 g (6.24 mmol) of hafnium(IV) chloride in 10 mL of methanol was slowly dropped into the mixture. The resulting mixture was stirred at room temperature for one hour for carrying out a reaction. After the reaction was complete, the reaction mixture was placed under reduced pressure to distill methanol off. To the residue were added 30 mL of hexane and 30 mL of water. The organic portion was taken out, dried over anhydrous sodium sulfate, and filtered. The filtrate was concentrated. The concentrated filtrate was placed under reduced pressure and distilled at 220° C., 23 Pa, to give 4.32 g (yield: 80%) of tetrakis (2-methoxy-3,5-octanedionato) hafnium(IV) as viscous yellow liquid.

The tetrakis(2-methoxy-3,5-octanedionato)hafnium(VI) is a new compound having the following characteristics:

IR (neat, cm$^{-1}$): 2962, 2932, 2873, 2822, 1598, 1528, 1430, 1211, 1120, 976, 795, 524 (the characteristic peak (1608 cm$^{-1}$) of β-diketone has disappeared, and a characteristic peak (1598 cm$^{-1}$) of β-diketonato appears), Elemental analysis: found: C, 50.1%; H, 7.03%; Hf, 20.6%. calculated ($C_{36}H_{60}O_{12}Hf$): C, 50.1%; H, 7.00%; Hf, 20.7%. MS (m/e): 693, 113, 59.

Example B-8

Preparation of tetrakis(2-methoxy-3,5-hexanedionato) hafnium (IV)—Hf (momd)$_4$

In a 100 mL-volume flask equipped with a stirrer, a thermometer and a dropping funnel was placed 9.40 g (48.7 mmol) of 28% sodium methoxide methanol solution. Into the ice-cooled solution was slowly dropped 7.00 g (48.9 mmol) of 2-methoxy-3,5-hexanedione (prepared by the method of Reference Example 7), and the mixture was stirred for 15 minutes. Subsequently, a solution of 3.90 g (12.2 mmol) of hafnium(IV) chloride in 20 mL of methanol was slowly dropped into the mixture. The resulting mixture was stirred at room temperature for one hour for carrying out a reaction. After the reaction was complete, the reaction mixture was placed under reduced pressure to distill methanol off. To the residue were added 20 mL of hexane and 20 mL of water. The organic portion was taken out, dried over anhydrous sodium sulfate, and filtered. The filtrate was concentrated. The concentrated filtrate was placed under reduced pressure and distilled at 190° C., 13.3 Pa, to give 3.73 g (yield: 41%) of tetrakis(2-methoxy-3,5-hexanedionato)hafnium(IV) as viscous yellow liquid.

The tetrakis(2-methoxy-3,5-hexanedionato)hafnium(VI) is a new compound having the following characteristics:

IR (neat, cm$^{-1}$): 2979, 2932, 2873, 2823, 1599, 1528, 1416, 1362, 1274, 1212, 1120, 1023, 794, 517 (the characteristic peak (1611 cm$^{-1}$) of β-diketone has disappeared, and a characteristic peak (1599 cm$^{-1}$) of β-diketonato appears).

Elemental analysis: found: C, 44.6%; H, 5.92%; Hf, 23.6%. calculated ($C_{28}H_{44}O_{12}Hf$): C, 44.8%; H, 5.90%; Hf, 23.8%. MS (m/e): 653, 609, 565, 59.

Example B-9

Preparation of tetrakis(2-methoxy-3,5-heptanedionato)hafnium(IV)—Hf(mohd)$_4$

In a 100 mL-volume flask equipped with a stirrer, a thermometer and a dropping funnel was placed 5.90 g (18.4 mmol) of hafnium(IV) chloride and 30 mL of methanol. Separately, 12.1 g (76.2 mmol) of 2-methoxy-3,5-heptanedione (prepared by the method of Reference Example 8) was slowly dropped into 18.0 g (75 mmol) of aqueous sodium hydroxide solution (5 mol/L) under cooling with ice. The resulting solution was dropped into the hafnium chloride methanol solution, and the mixture was stirred at room temperature for 30 minutes for carrying out a reaction. After the reaction was complete, 50 mL of methylcyclohexane and 50 mL of water were added. The organic portion was taken out, dried over anhydrous sodium sulfate, and filtered. The filtrate was concentrated. The concentrated filtrate was placed under reduced pressure and distilled at 205° C., 18.6 Pa, to give 12.6 g (yield: 85%) of tetrakis(2-methoxy-3,5-heptanedionato)hafnium(IV) as viscous yellow liquid.

The tetrakis(2-methoxy-3,5-heptanedionato)hafnium (VI) is a new compound having the following characteristics:

IR (neat, cm$^{-1}$): 2978, 2934, 2877, 2823, 1594, 1529, 1431, 1328, 1211, 1120, 1072, 808, 521 (the characteristic peak (1610 cm$^1$-1) of β-diketone has disappeared, and a characteristic peak (1594 cm$^{-1}$) of β-diketonato appears), Elemental analysis: found: C, 47.4%; H, 6.50%; Hf, 22.1%. calculated ($C_{32}H_{52}O_{12}Hf$): C, 47.6%; H, 6.49%; Hf, 22.1%. MS (m/e): 681, 651, 621, 367, 221, 128, 99, 59.

Examples B-10 to B-21

Deposition Tests

Preparation of Metal Oxide Film

The deposition experiment by the CVD method was performed using a metal complex compound prepared in Examples B-1 to B-9 (chromium complex compound (Cr (mopd)$_3$), manganese complex compound (Mn(mopd)$_2$), nickel complex compound (Ni(mopd)$_2$), cobalt complex compound (Co(mopd)$_2$), titanium complex compound (Ti (mopd)$_4$), zirconium complex compound (Zr(mood)$_4$), or hafnium complex compound (Hf(mood)$_4$, Hf(momd)$_4$, or Hf(mohd)$_4$) to evaluate the film-forming property.

The experiment for evaluation was performed using an apparatus illustrated in FIG. 1 when oxygen was employed for the formation of a metal oxide film. Otherwise, the experiment for evaluation was performed using an apparatus illustrated in FIG. 2 when steam was employed for the formation of a metal oxide film.

The metal complex compound 20 placed in a vaporizer (glass ampul) 3 is heated by a heater 10B to vaporize. The vapor passes through a mass flow controller 1A and comes out of the vaporizer 3 together with a helium gas which is supplied after heating in a pre-heater 10A. The vapor having come out of the vaporizer 3 enters a reactor 4 together with an oxygen gas which is supplied through a mass flow controller 1B and a stop valve 2 (FIG. 1) or a helium gas containing steam supplied through the mass flow controller 1B and a cooled water 8. The pressure in the reactor is regulated to a predetermined value by on-off of a valve 6 arranged in a position prior to the vacuum pump and monitored by means of a pressure gauge 5. The center portion of the glass reactor is so constituted that it can be heated by a heater 10C. The metal complex compound supplied into the reactor oxidatively decomposes on a surface of a substrate 21 for receiving deposition which is arranged in the reactor at the central position and heated to a predetermined temperature by the heater 10C, so that a metal oxide film deposits on the substrate 21. The gas coming out of the reactor 4 is exhausted into the atmosphere through a trap 7 and a vacuum pump.

The deposition conditions are set forth below.

Examples B-10 to B-16

The Deposition Apparatus of FIG. 1 was Employed

Flow rate of He carrier: 30 mL/min.
Flow rate of oxygen: 20 mL/min.
Substrate: SiO$_2$/Si (size: 7 mm×40 mm)
Temperature of substrate: 400° C.
Pressure in reactor: 5,320 Pa
Deposition period: 30 minutes Examples B-17 to B-18

The Deposition Apparatus of FIG. 1 was Employed

Flow rate of He carrier: 30 mL/min.
Flow rate of oxygen: 80 mL/min.
Substrate: SiO$_2$/Si (size: 7 mm×40 mm)
Temperature of substrate: 450° C.
Pressure in reactor: 7,980 Pa
Deposition period: 60 minutes Examples B-19 to B-21

Figure 2:
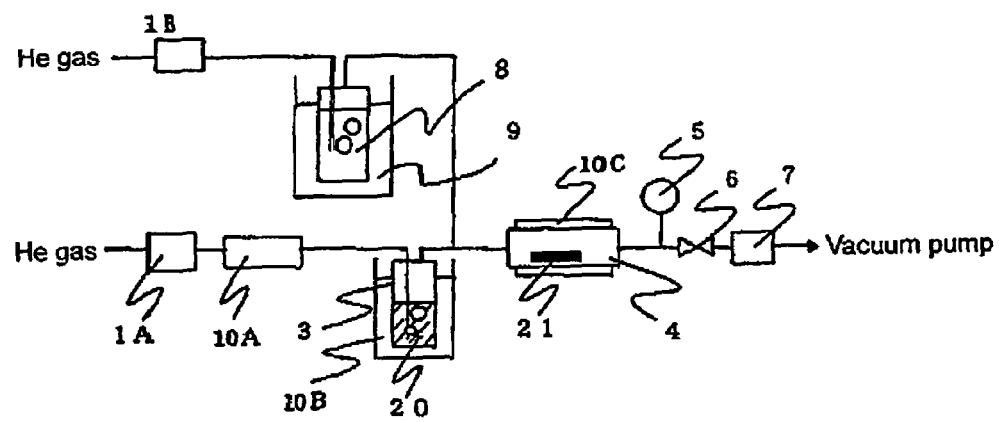
FIG. 2 illustrates a constitution of a deposition apparatus for preparing a metal oxide film using steam.
1A: mass flow controller
1B: mass flow controller
2: stop valve
3: vaporizer
4: reactor
5: pressure gauge
6: valve
7: trap
8: water
9: cooler
10A: pre-heater
10B: heater for vaporizer
10C: heater for reactor
20: fuzed liquid or solution of metal complex
21: substrate

The Deposition Apparatus of FIG. 2 was Employed

Flow rate of He carrier for supplying metal complex compound: 60 mL/min.
Flow rate of He carrier for supplying steam: 60 mL/min.
Substrate: SiO$_2$/Si (size: 7 mm×40 mm)
Temperature of substrate: 300° C.

Pressure in reactor: 2,660 Pa

Deposition period: 60 minutes

The results of deposition (film property and analysis of product were performed by XPS analysis) are set forth in Tables 5 and 6.

TABLE 5

|  | Metal complex compound | Vaporizing temperature | Film property (film thickness) |
|---|---|---|---|
| Ex. B-10 | Cr(mopd)$_3$ | 170° C. | Chromium oxide (40 nm) |
| Ex. B-11 | Mn(mood)$_2$ | 180° C. | Manganese oxide (35 nm) |
| Ex. B-12 | Ni(mood)$_2$ | 150° C. | Nickel oxide (35 nm) |
| Ex. B-13 | Co(mopd)$_2$ | 150° C. | Cobalt oxide (40 nm) |
| Ex. B-14 | Ti(mopd)$_4$ | 150° C. | Titanium oxide (45 nm) |
| Ex. B-15 | Zr(mood)$_4$ | 170° C. | Zirconium oxide (40 nm) |
| Ex. B-16 | Hf(mood)$_4$ | 170° C. | Hafnium oxide (35 nm) |
| EX. B-17 | Hf(momd)$_4$ | 140° C. | Hafnium oxide (40 nm) |
| Ex. B-18 | Hf(mohd)$_4$ | 140° C. | Hafnium oxide (40 nm) |

TABLE 6

|  | Metal complex compound | Vaporizing temperature | Film property (film thickness) |
|---|---|---|---|
| Ex. B-19 | Hf(mohd)$_4$ | 140° C. | Hafnium oxide (30 nm) |
| Ex. B-20 | Zr(mood)$_4$ | 140° C. | Zirconium oxide (30 nm) |
| Ex. B-21 | Ti(mopd)$_4$ | 120° C. | Titanium oxide (35 nm) |

The results shown in Tables 5 and 6 indicate that the metal complex compounds of the invention have a good film-foaming property.

Reference Example 9

Preparation of 2-methoxy-3,5-heptanedione (mohd)

In a 200 mL-volume flask equipped with a stirrer, a thermometer and a dropping funnel was placed 25.0 g (223 mmol) of potassium t-butoxide, and the flask was purged with argon. Then, 100 mL of methylcyclohexanone was placed in the flask. Subsequently, 12.5 g (106 mmol) of methyl 2-methoxypropionate (prepared by the method of Reference Example 1) was dropped under cooling with ice, and further 7.70 g (107 mmol) of 2-butanone was slowly dropped. The mixture was cooled to 10° C. and stirred for 30 minutes for carrying out a reaction. After the reaction was complete, 70 mL of water was placed in the flask under cooling with ice. The aqueous portion was taken out, neutralized with acetic acid, and subjected to extraction with methylcyclohexane. The methylcyclohexane extract was washed with water, dried over anhydrous sodium sulfate, and filtered. The filtrate was concentrated and distilled under reduced pressure (77° C., 1.26 kPa) to give 10.4 g (yield: 62%) of 2-methoxy-3,5-heptanedione as colorless liquid.

Example C-1

Preparation of bis(2-methoxy-6-methyl-3,5-heptanedionato)copper(II)—Cu(mopd)$_2$ In a 100 mL-volume flask equipped with a stirrer, a thermometer and a dropping funnel were placed 0.906 g (9.29 mmol) of copper(II) hydroxide and 10 mL of mesitylene chloride. Subsequently, 1.57 g (9.12 mmol) of 2-methoxy-6-methyl-3,5-heptanedione (prepared by the method of Reference Example 2) was slowly dropped. The resulting mixture was stirred at room temperature for 90 minutes for carrying out a reaction. After the reaction was complete, the reaction mixture was concentrated. The concentrate was then distilled under reduced pressure at 170° C., 63 Pa, to give 1.50 g (yield: 81%) of bis(2-methoxy-6-methyl-3,5-heptanedionato)copper(II) as violet solid.

The bis(2-methoxy-6-methyl-3,5-heptanedionato)-copper (II) is a new compound having the following characteristics:

m.p.: 107° C. IR (neat, cm$^{-1}$); 3436 (br), 2970, 2933, 2874, 2827, 1572, 1513, 1430, 1334, 1242, 1114, 1057, 914, 811, 580 (the characteristic peak (1607 cm$^{-1}$) of β-diketone has disappeared, and a characteristic peak (1572 cm$^{-1}$) of β-diketonato appears), Elemental analysis: found: C, 53.7%; H, 7.49%; Cu, 15.6%. calculated ($C_{18}H_{30}O_6Cu$): C, 53.3%; H, 7.45%; Cu, 15.7%. MS (m/e): 405, 362, 287, 235, 175, 113, 59

Example C-2

Preparation of bis(2-methoxy-3,5-octane-dionato) copper(II)—Cu(mood)$_2$

In a 100 mL-volume flask equipped with a stirrer, a thermometer and a dropping funnel were placed 10.1 g (58.4 mmol) of 2-methoxy-3,5-octanedione (prepared by the method of Reference Example 3) and 30 mL of toluene. Subsequently, 24.0 g (7.48 mmol) of an aqueous copper(II) acetate solution (5.66 wt. %) was slowly dropped. The resulting mixture was stirred at room temperature for 20 minutes for carrying out a reaction. After the reaction was complete, the toluene portion was taken out. Thereafter, this procedure was repeated twice. The toluene portion was then washed with water and concentrated under reduced pressure. The concentrate was then distilled under reduced pressure at 170° C., 27 Pa, to give 10.6 g (yield: 87%) of bis(2-methoxy-3,5-octanedionato)copper(II) as violet solid.

The bis(2-methoxy-3,5-octanedionato)copper(II) is a new compound having the following characteristics:

m.p.: 78° C. IR (neat, cm$^{-1}$): 3431 (br), 2964, 2933, 2873, 2821, 1568, 1518, 1442, 1366, 1206, 1127, 970, 802, 553, 480 (the characteristic peak (1608 cm$^{-1}$) of β-diketone has disappeared, and a characteristic peak (1568 cm$^{-1}$) of β-diketonato appears), Elemental analysis: found: C, 53.8%; H, 7.43%; Cu, 15.7%. calculated ($C_{18}H_{30}O_6Cu$): C, 53.3%; H, 7.45%; Cu, 15.7%. MS (m/e): 405, 346, 287, 235, 175, 113, 59, 28.

Example C-3

Preparation of bis(2-methoxy-3,5-heptane-dionato) copper(II)—Cu(mohd)$_2$

In a 100 mL-volume flask equipped with a stirrer, a thermometer and a dropping funnel were placed 5.03 g (31.8 mmol) of 2-methoxy-3,5-heptanedione (prepared by the method of Reference Example 9) and 40 mL of toluene. Subsequently, 33.0 g (16.5 mmol) of an aqueous copper(II) acetate solution (9.09 wt.) was slowly dropped. The resulting mixture was stirred at room temperature for 60 minutes for carrying out a reaction. After the reaction was complete, the organic portion was taken out, and concentrated under reduced pressure. The concentrate was then distilled under reduced pressure at 160° C., 17 Pa, to give 4.06 g (yield: 77%) of bis(2-methoxy-3,5-heptane-dionato)copper(II) as violet solid.

The bis(2-methoxy-3,5-heptanedionato)copper(II) is a new compound having the following characteristics:

m.p.: 104° C. IR (neat, cm$^{-1}$): 3432 (br), 2978, 2935, 2879, 2826, 1569, 1518, 1443, 1343, 1207, 1127, 1074, 808, 551, 434 (the characteristic peak (1610 cm$^{-1}$) of β-diketone has disappeared, and a characteristic peak (1569 cm$^{-1}$) of βdiketonato appears), Elemental analysis: found: C, 50.8%; H, 6.98%; Cu, 16.8%. calculated ($C_{16}H_{26}O_6Cu$): C, 50.9%; H, 6.93%; Cu, 16.8%. MS (m/e): 377, 318, 259, 221, 161, 999, 59.

Examples C-4 to C-6

Deposition Tests

Preparation of Copper Film

The deposition experiment by the CVD method was performed using a copper complex compound prepared in Examples C-1 to C-3 (Cu(mopd)$_2$, (Cu(mood)$_2$), or (Cu(mohd)$_2$), to evaluate the film-forming property. The deposition experiment was carried out using the apparatus of FIG. 1, but a hydrogen gas was employed as the reactive gas in place of the oxygen gas.

The deposition conditions are set forth below.
Flow rate of He carrier: 30 mL/min.
Flow rate of hydrogen: 120 mL/min.
Substrate: SiO$_2$/Si (size: 7 mm×40 mm)
Temperature of substrate: 250° C.
Pressure in reactor: 7,980 Pa
Deposition period: 30 minutes The results of deposition (film property and analysis of product were performed by XPS analysis) are set forth in Table 7.

TABLE 7

| | Metal complex compound | Vaporizing temp. | Film (thickness) (specific resistance) |
|---|---|---|---|
| Ex. C-4 | Cu(mopd)$_2$ | 140° C. | copper (110 nm) 3.5 |
| Ex. C-5 | Cu(mood)$_2$ | 140° C. | copper (100 nm) 3.5 |
| Ex. C-6 | Cu(mohd)$_2$ | 140° C. | copper (120 nm) 3.2 |

Remarks:
Each of the formed copper films showed a metallic luster and had a uniform smooth surface.

The results shown in Table 7 indicate that the metal complex compounds of the invention have a good film-forming property.

Example D-1

Preparation of tris(2-methoxy-6-methyl-3,5-heptanedionato)lanthanum(III)—La(mopd)$_3$ In a 100-mL-volume flask equipped with a stirrer, a thermometer and a dropping funnel were placed 1.0 (3.16 mmol) of lanthanum(III) acetate, 20 mL of tetrahydrofuran, and 5 mg (21.7 mmol) of aqueous sodium hydroxide solution (10 wt. %). Subsequently, 2.0 g (11.6 mmol) of 2-methoxy-6-methyl-3,5-heptanedione (prepared by the method of Reference Example 2) was slowly dropped. The resulting mixture was stirred at room temperature for 90 minutes for carrying out a reaction. After the reaction was complete, the reaction mixture was filtered. The filtrate was washed with water and concentrated under reduced pressure. The concentrate was then distilled under reduced pressure at 230° C., 26.6 Pa, to give 0.93 g (yield: 45%) of tris(2-methoxy-6-methyl-3,5-heptanedionato)-lanthanum(III) as viscous colorless liquid.

The tris(2-methoxy-6-methyl-3,5-heptanedionato)-lanthanum(III) is a new compound having the following characteristics:

m.p.: 21° C. IR (neat, cm$^{-1}$): 3477 (br), 2968, 2931, 2870, 2827, 1603, 1525, 1483, 1371, 1331, 1209, 1151, 1114, 1060, 1019, 955, 910, 865, 811, 782, 553, Elemental analysis: found: C, 50.2%; H, 6.91%; La, 21.7%. calculated ($C_{27}H_{45}O_9La$): C, 49.7%; H, 6.95%; La, 21.3%. MS (m/e): 675, 481, 398, 310, 173, 113, 59.

$^1$H-NMR (CDCl$_3$, δ (ppm)): 1.24 (3H, d), 1.35 (3H, d), 2.2-2.3 (1H, m), 3.33 (3H, s), 3.58-3.65 (1H, q), 5.18 (1H, s).

Example D-2

Preparation of tris(2-methoxy-6-methyl-3,5-heptanedionato)samarium(III)—Sm(mopd)$_3$ In a 100 mL-volume flask equipped with a stirrer, a thermometer and a dropping funnel were placed 1.0 g (2.50 mmol) of samarium(III) acetate, 20 mL of tetrahydrofuran, and 5 mg (21.7 mmol) of aqueous sodium hydroxide solution (10 wt. %). Subsequently, 1.72 g (10.0 mmol) of 2-methoxy-6-methyl-3,5-heptanedione (prepared by the method of Reference Example 2) was slowly dropped. The resulting mixture was stirred at room temperature for 90 minutes for carrying out a reaction. After the reaction was complete, the reaction mixture was filtered. The filtrate was washed with water and concentrated under reduced pressure. The concentrate was then distilled under reduced pressure at 230° C., 26.6 Pa, to give 0.58 g (yield: 35%) of tris(2-methoxy-6-methyl-3,5-heptanedionato)-samarium(III) as viscous yellow liquid.

The tris(2-methoxy-6-methyl-3,5-heptanedionato)-samarium(III) is a new compound having the following characteristics:

m.p.: 25° C. IR (neat, cm$^{-1}$): 2968, 2931, 2870, 2825, 1605, 1525, 1495, 1371, 1331, 1210, 1113, 1020, 910, 804, 783, Elemental analysis: found: C, 48.5%; H, 6.87%; Sm, 22.1%. calculated ($C_{27}H_{45}O_9Sm$): C, 48.8%; H, 6.83%; Sm, 22.6%. MS (m/e): 688, 494, 368, 324, 113, 59.

$^1$H-NMR (CDCl$_3$, δ (ppm)): 0.87-0.99 (3H, brd), 1.12 (6H, m), 2.5 (1H, m), 2.9 (3H, brs), 3.29-3.65 (1H, brs), 5.60-5.77 (1H, br).

Example D-3

Preparation of tris(2-methoxy-3,5-octane-dionato)lanthanum(III)—La(mood)$_3$

In a 100 mL-volume flask equipped with a stirrer, a thermometer and a dropping funnel were placed 1.0 g (3.16 mmol) of lanthanum(III) acetate, 20 mL of tetrahydro-furan, and 5 mg (21.7 mmol) of aqueous sodium hydroxide solution (10 wt. %). Subsequently, 2.0 g (11.6 mmol) of 2-methoxy-3,5-octanedione (prepared by the method of Reference Example 6) was slowly dropped. The resulting mixture was stirred at room temperature for 90 minutes for carrying out a reaction. After the reaction was complete, the reaction mixture was filtered. The filtrate was washed with water and concentrated under reduced pressure. The concentrate was then distilled under reduced pressure at 230° C., 26.6 Pa, to give 0.55 g (yield: 27%) of tris(2-methoxy-3,5-octanedionato)lanthanum(III) as viscous colorless liquid.

The tris(2-methoxy-3,5-octanedionato)lanthanum(III) is a new compound having the following characteristics:

m.p.: 10° C. IR (neat, $cm^{-1}$): 2961, 2931, 2873, 2826, 1600, 1518, 1479, 1338, 1209, 1116, 1019, 960, 789, Elemental analysis: found: C, 49.5%; H, 6.99%; La, 20.9%. calculated ($C_{27}H_{45}O_9La$): C, 49.7%; H, 6.95%; La, 21.3%. MS (m/e): 675, 481, 398, 142, 113, 59. $^1$H-NMR ($CDCl_3$, δ (ppm)): 0.86 (3H, t), 1.23 (3H, d), 1.48-1.58 (2H, m), 2.05 (2H, t), 3.32 (3H, s), 3.57-3.64 (1H, q), 5.19 (1H, s).

Example D-4

Deposition Test

Preparation of Lanthanum Oxide Film

The deposition experiment by the CVD method was performed using a lanthanum complex compound prepared in Example D-1 (La(mopd)$_3$), to evaluate the film-forming property. The deposition experiment was carried out using the apparatus of FIG. 1.

The deposition conditions are set forth below.
Flow rate of He carrier: 30 mL/min.
Flow rate of oxygen: 120 mL/min.
Substrate: $SiO_2$/Si (size: 7 mm×40 mm)
Temperature of substrate: 450° C.
Pressure in reactor: 7,980 Pa
Deposition period: 30 minutes The results of deposition (film property and analysis of product were performed by XPS analysis) are set forth in Table 8.

TABLE 8

|  | Metal complex compound | Vaporizing temperature | Film property (film thickness) |
|---|---|---|---|
| Ex. D-4 | La(mopd)$_2$ | 180° C. | lanthanum oxide (30 nm) |

The results shown in Table 8 indicate that the metal complex compound of the invention has a good film-forming property.

Example E-1

Preparation of bis(2-methoxy-3,5-heptane-dionato) lead(II)—Pb(mohd)$_2$

In a 100 mL-volume flask equipped with a stirrer, a thermometer and a dropping funnel were placed a suspension of 8.04 g (28.9 mmol) of lead(II) chloride and 40 mL of methylcyclohexanone. Into the suspension was slowly dropped 10.35 g (60.1 mmol) of 2-methoxy-3,5-heptanedione (prepared by the method of Reference Example 8) at room temperature. Subsequently, into the ice-cooled mixture was dropped 14.5 g (NaOH 61 mmol) of aqueous 17% sodium hydroxide solution. The resulting mixture was stirred at room temperature for one hour for carrying out a reaction. After the reaction was complete, the organic portion was taken out, dried over anhydrous sodium sulfate, and filtered. The filtrate was concentrated under reduced pressure. The concentrate was then distilled under reduced pressure at 190° C., 20 Pa, to give 7.57 g (yield: 50%) of bis(2-methoxy-3,5-heptanedionato)lead(II) as viscous yellow liquid.

The bis(2-methoxy-3,5-heptanedionato)lead(II) is a new compound having the following characteristics:

IR (neat, $cm^{-1}$): 2976, 2934, 2877, 2822, 1594, 1516, 1420, 1371, 1335, 1302, 1210, 1117, 1068, 1016, 944, 882, 821, 515 (the characteristic peak (1610 $cm^{-1}$) of O-diketone has disappeared, and a characteristic peak (1594 $cm^{-1}$) of β-diketonato appears), Elemental analysis: found: C, 36.6%; H, 5.03%; Pb, 39.5%. calculated ($C_{16}H_{26}O_6Pb$): C, 36.8%; H, 5.02%; Pb, 39.7%. MS (m/e): 522, 463, 311, 99, 59.

Example E-2

Preparation of tris(2-methoxy-3,5-hexane-dionato) indium(III)—In(momd)$_3$

In a 100 mL-volume flask equipped with a stirrer, a thermometer and a dropping funnel was placed 11.7 g (NaOH 43.5 mmol) of aqueous 14.8% sodium hydroxide solution. Into the ice-cooled solution was slowly dropped 6.51 g (45.5 mmol) of 2-methoxy-3,5-hexanedione (prepared by the method of Reference Example 7). The resulting mixture was stirred for 5 minutes. Subsequently, a solution of 4.04 g (13.8 mmol) of indium(III) chloride tetrahydrate in 30 mL of methanol was slowly dropped, and the resulting mixture was stirred at water temperature for 30 minutes for carrying out a reaction. After the reaction was complete, 50 mL of methylcyclohexane and 20 mL of water were added. Then, the organic portion was taken out, dried over anhydrous sodium sulfate, and filtered. The filtrate was concentrated under reduced pressure. The concentrate was then distilled under reduced pressure at 180° C., 15 Pa, to give 5.91 g (yield: 79%) of tris(2-methoxy-3,5-hexanedionato)indium(III) as viscous pale yellow liquid.

The tris(2-methoxy-3,5-hexanedionato)indium(III) is a new compound having the following characteristics:

IR (neat, $cm^{-1}$): 2981, 2933, 2882, 2824, 1574, 1523, 1412, 1387, 1265, 1212, 1119, 1025, 909, 806, 538 (the characteristic peak (1611 $cm^{-1}$) of β-diketone has disappeared, and a characteristic peak (1574 $cm^{-1}$) of β-diketonato appears), Elemental analysis; found: C, 46.6%; H, 6.20%; In, 21.0%. calculated ($C_{21}H_{33}O_9In$): C, 46.3%; H, 6.11%; In, 21.1%. MS (m/e): 544, 514, 401, 289, 199, 115, 59.

Example E-3

Preparation of tetrakis(2-methoxy-3,5-hexanedionato)zirconium(IV)—Zr(momd)$_4$

In a 100 mL-volume flask equipped with a stirrer, a thermometer and a dropping funnel was placed 29.2 g (NaOH 78.8 mmol) of aqueous 10.8% sodium hydroxide solution. Into the ice-cooled solution was slowly dropped 12.1 g (83.6 mmol) of 2-methoxy-3,5-hexanedione (prepared by the method of Reference Example 7). The resulting mixture was stirred for 5 minutes. Subsequently, the above-mentioned aqueous solution was slowly dropped into a solution of 4.33 g (18.6 mmol) of zirconium(IV) chloride in 40 mL of methanol, and the resulting mixture was stirred for 30 minutes for carrying out a reaction. After the reaction was complete, 40 mL of methylcyclohexane and 50 mL of water were added. Then, the organic portion was taken out, dried over anhydrous sodium sulfate, and filtered. The filtrate was concentrated under reduced pressure. The concentrate was then distilled under reduced pressure at 220° C., 24 Pa, to give 5.78 g (yield: 47%) of tetrakis(2-methoxy-3,5-hexanedionato)zirconium (IV) as viscous colorless liquid.

The tetrakis(2-methoxy-3,5-hexanedionato) zirconium (IV) is a new compound having the following characteristics:

IR (neat, cm$^{-1}$): 2979, 2932, 2873, 2823, 1597, 1526, 1414, 1361, 1272, 1211, 1120, 1023, 794, 516, 419 (the characteristic peak (1613 cm$^{-1}$) of β-diketone has disappeared, and a characteristic peak (1597 cm$^{-1}$) of β-diketonato appears), Elemental analysis: found: C, 50.9%; H, 6.71%; Zr, 13.6%. calculated ($C_{28}H_{44}O_{12}Zr$): C, 50.7%; H, 6.68%; Zr, 13.7%. MS (m/e): 519, 193, 109, 85, 59.

Example E-4

Preparation of bis(2'-methoxy-3,5-octane-dionato) nickel(II)—Ni(mood)$_2$

In a 100 mL-volume flask equipped with a stirrer, a thermometer and a dropping funnel were placed 14.1 g (73.1 mmol) of 28% sodium methoxide methanol solution and 15 mL of methanol. Into the ice-cooled solution was slowly dropped 12.6 g (73.2 mmol) of 2-methoxy-3,5-octanedione (prepared by the method of Reference Example 6), and the mixture was stirred for 5 minutes. Subsequently, a solution of 10.0 g (11.5 mmol) of nickel(II) chloride hexahydrate in 30 mL of methanol was slowly dropped into the ice-cooled mixture. The resulting mixture was stirred at room temperature for one hour for carrying out a reaction. After the reaction was complete, the reaction mixture was placed under reduced pressure to distill methanol off. To the residue were added 50 mL of methylene chloride and 50 mL of water. The organic portion was taken out, dried over anhydrous sodium sulfate, and filtered. The filtrate was concentrated. The concentrated filtrate was placed under reduced pressure and distilled at 230° C., 40 Pa, to give 7.20 g (yield: 43%) of bis(2-methoxy-3,5-octanedionato)nickel(II) as dark green solid.

The bis(2-methoxy-3,5-octanedionato)nickel(II) is a new compound having the following characteristics:

IR (neat, cm$^{-1}$): 3415 (br), 2963, 2933, 2874, 2823, 1598, 1520, 1431, 1334, 1211, 1117, 1017, 960, 795, 558 (the characteristic peak (1608 cm$^{-1}$) of β-diketone has disappeared, and a characteristic peak (1598 cm$^{-1}$) of β-diketonato appears), Elemental analysis: found: C, 53.7%; H, 7.59%; Ni, 14.5%. calculated ($C_{18}H_{30}O_6Ni$): C, 53.9%; H, 7.54%; Ni, 14.6%. MS (m/e): 400, 341, 113, 59.

Example E-5

Preparation of tetrakis(2-methoxy-6-methyl-3,5-heptanedionato)hafnium(IV)—Hf(mopd)$_4$ In a 100 mL-volume flask equipped with a stirrer, a thermometer and a dropping funnel were placed 3.95 g (20 mmol) of 28% sodium methoxide methanol solution and 10 mL of methanol. Into the ice-cooled solution was slowly dropped 21.2 g (3.65 mmol) of 2-methoxy-6-methyl-3,5-heptanedione (prepared by the method of Reference Example 2), and the mixture was stirred for 5 minutes. Subsequently, a solution of 1.60 g (5.00 mmol) of hafnium(IV) chloride in 6 mL of methanol was slowly dropped into the ice-cooled mixture. The resulting mixture was stirred at room temperature for one hour for carrying out a reaction. After the reaction was complete, the reaction mixture was placed under reduced pressure to distill methanol off. To the residue was added 10 mL of hexane. The resulting mixture was filtered, and the filtrate was concentrated. The concentrated filtrate was placed under reduced pressure and distilled at 220° C., 24 Pa, to give 3.00 g (yield: 70%) of bis(2-methoxy-6-methyl-3,5-heptanedionato) hafnium(IV) as pale yellow solid.

The bis(2-methoxy-6-methyl-3,5-heptanedionato)-hafnium(IV) is a new compound having the following characteristics:

m.p.: 160° C., IR (neat, cm$^{-1}$): 3414 (br), 2974, 2932, 2871, 2823, 1582, 1534, 1433, 1329, 1240, 1210, 1120, 1060, 969, 915, 797, 544 (the characteristic peak (1607 cm$^{-1}$) of β-diketone has disappeared, and a characteristic peak (1582 cm$^{-1}$) of β-diketonato appears), Elemental analysis: found: C, 50.3%; H, 7.10%; Hf, 20.5%. calculated ($C_{36}H_{60}O_{12}Hf$): C, 50.1%; H, 7.00%; Hf, 20.7%. MS (m/e): 693, 113, 59.

Example E-6

Preparation of tetrakis(2-methoxy-6-methyl-3,5-heptanedionato)zirconium(IV)—Zr(mopd)$_4$ In a 100 mL-volume flask equipped with a stirrer, a thermometer and a dropping funnel were placed 4.70 g (24.4-mmol) of 28% sodium methoxide methanol solution and 10 mL of methanol. Into the ice-cooled solution was slowly drooped 4.20 g (24.4 mmol) of 2-methoxy-6-methyl-3,5-heptanedione (prepared by the method of Reference Example 2), and the mixture was stirred for 5 minutes. Subsequently, a solution of 1.38 g (5.92 mmol) of zirconium (IV) chloride in 4 mL of methanol was slowly dropped into the ice-cooled mixture. The resulting mixture was stirred at room temperature for one hour for carrying out a reaction. After the reaction was complete, the reaction mixture was placed under reduced pressure to distill methanol off. To the residue were added 30 mL of hexane and 30 mL of water. The organic portion was taken out, dried over anhydrous sodium sulfate, and filtered. The filtrate was concentrated. The concentrated filtrate was placed under reduced pressure and distilled at 220° C., 25 Pa, to give 1.27 g (yield: 28%) of bis(2-methoxy-6-methyl 3,5-heptanedionato)zirconium(IV) as pale yellow solid.

The bis(2-methoxy-6-methyl-3,5-heptanedionato)-zirconium(IV) is a new compound having the following characteristics:

m.p.: 165° C., IR (neat, cm$^{-1}$): 2974, 2932, 2871, 2823, 1580, 1533, 1431, 1329, 1238, 1210, 1120, 1060, 969, 914, 797, 575, 542 (the characteristic peak (1607 cm$^{-1}$) of β-diketone has disappeared, and a characteristic peak (1580 cm$^{-1}$) of β-diketonato appears), Elemental analysis: found: C, 55.3%; H, 7.72%; Zr, 11.3%. calculated ($C_{36}H_{60}O_{12}Zr$): C, 55.7%; H, 7.79%; Zr, 11.8%. MS (m/e): 603, 113, 59.

Example E-7

Preparation of tris(2-methoxy-6-methyl-3,5-heptanedionato)yttrium(IV)—Y(mopd)$_3$ In a 100 mL-volume flask equipped with a stirrer, a thermometer and a dropping funnel were placed 5.12 g (26.5 mmol) of 28% sodium methoxide methano solution and 10 mL of methanol. Into the ice-cooled solution was slowly dropped 4.60 g (26.7 mmol) of 2-methoxy-6-methyl-3,5-heptanedione (prepared by the method of Reference Example 2), and the mixture was stirred for 5 minutes. Subsequently, a solution of 2.62 g (8.64 mmol) of yttrium (III) chloride hexahydrate in 20 mL of methanol was slowly dropped into the mixture at room temperature. The resulting mixture was stirred at room temperature for one hour for carrying out a reaction. After the reaction was complete, the reaction mixture was placed under reduced pressure to distill methanol off. To the residue were added 30 mL of hexane and 30 mL of water. The organic portion was taken out, dried over anhydrous sodium sulfate, and filtered. The filtrate was concentrated. The concentrated filtrate was placed under reduced pressure sure and distilled at 220° C., 35 Pa, to give 2.43 q (yield: 47%) of tris(2-methoxy-6-methyl-3,5-heptanedionato)-yttrium(III) as glassy orange solid.

The tris(2-methoxy-6-methyl-3,5-heptanedionato)-yttrium(III) is a new compound having the following characteristics:

m.p.: 38° C., IR (neat, cm$^{-1}$): 3435 (br), 2973, 2932, 2871, 2822, 1608, 1531, 1432, 1331, 1211, 1152, 1118, 1022, 912, 787, 559, Elemental analysis: found: C, 55.3%; H, 7.72%; Y, 11.3%. calculated ($C_{27}H_{45}O_9Y$): C, 53.8%; H, 7.53%; Y, 14.8%. MS (m/e): 625, 602, 571, 559, 543, 431, 339, 259, 113, 59.

Reference Example 10

Preparation of 2-methoxy-3,5-hexanedione (momd)

In a 300 mL-volume flask equipped with a stirrer, a thermometer and a dropping funnel was placed 29.0 g (258 mmol) of potassium t-butoxide, and the flask was purged with argon. Then, 120 mL of methylcyclohexanone was placed in the flask. Subsequently, 15.0 g (127 mmol) of methyl 2-methoxypropionate (prepared by the method of Reference Example 1) was dropped under cooling with ice, and further 7.40 g (127 mmol) of acetone was slowly dropped. The mixture was cooled to 10° C. and stirred for 30 minutes for carrying out a reaction. After the reaction was complete, 1,200 mL of water was placed in the flask under cooling with ice. The aqueous portion was taken out, neutralized with acetic acid, and subjected to extraction with methylcyclohexane. The methylcyclohexane extract was washed with water, dried over anhydrous sodium sulfate, and filtered. The filtrate was concentrated and distilled under reduced pressure (66° C., 1.38 kPa) to give 9.63 g (yield: 53%) of 2-methoxy-3,5-hexanedione as colorless liquid.

The 2-methoxy-3,5-hexanedione had the following characteristics:

$^1$H-NMR (CDCl$_3$, δ (ppm)): 1.29 (0.3H, d), 1.35 (2.7H, d), 2.11 (2.7H, s), 2.26 (0.3H, s), 3.36 (2.7H, s), 3.37 (0.3H, s), 3.64 (0.2H, s), 3.70-3.77 (1H, m), 5.80 (0.9H, s), 15.3 (0.9H, s), IR (neat, cm$^{-1}$): 2987, 2937, 2828, 1611 (br), 1451, 1368, 1337, 1239, 1211, 1119, 1058, 1018, 903, 801, 814 (the peak at 1611 cm$^{-1}$ is a characteristic peak of β-diketone), MS (m/e): 114, 85, 59, 43.

Examples E-8 to E-14

Deposition Tests

Preparation of Metal Oxide Film

The deposition experiment by the CVD method was performed using a metal complex compound prepared in Examples E-1 to E-7, to evaluate the film-forming property. The deposition experiment was carried out using the apparatus of FIG. 1.

The deposition conditions are set forth below.

Example E-8

Helium is Supplied Together with Oxygen to Dilute Oxygen

Flow rate of He carrier: 15 mL/min.
Flow rate of oxygen: 80 mL/min.
Flow rate of He (for oxygen dilution): 105 mL/min.
Substrate: SiO$_2$/Si (size: 7 mm×40 mm)
Temperature of substrate: 400° C.
Pressure in reactor: 7,980 Pa
Deposition period: 60 minutes Examples E-9, E-12, and E-13

Flow rate of He carrier: 30 mL/min.
Flow rate of oxygen: 20 mL/min.
Substrate: SiO$_2$/Si (size: 7 mm×40 mm)
Temperature of substrate: 400° C.
Pressure in reactor: 5,320 Pa
Deposition period: 30 minutes Example E-10

Helium is Supplied Together with Oxygen to Dilute Oxygen

Flow rate of He carrier: 30 mL/min.
Flow rate of oxygen: 80 mL/min.
Flow rate of He (for oxygen dilution): 90 mL/min
Substrate: SiO$_2$/Si (size: 7 mm×40 mm)
Temperature of substrate: 400° C.
Pressure in reactor: 19.9 kPa
Deposition period: 60 minutes Example E-11

Helium is Supplied Together with Oxygen to Dilute Oxygen

Flow rate of He carrier: 60 mL/min.
Flow rate of oxygen: 80 mL/min.
Flow rate of He (for oxygen dilution): 60 mL/min.
Substrate: SiO$_2$/Si (size: 7 mm×40 mm)
Temperature of substrate: 400° C.
Pressure in reactor: 7,980 Pa
Deposition period: 60 minutes Example E-14

Flow rate of He carrier: 30 mL/min.
Flow rate of oxygen: 20 mL/min.
Substrate: SiO$_2$/Si (size: 7 mm×40 mm)
Temperature of substrate: 450° C.
Pressure in reactor: 5,320 Pa
Deposition period: 30 minutes The results of deposition (film property and analysis of product were performed by XPS analysis) are set forth in Table 9.

TABLE 9

|  | Metal complex compound | Vaporizing temperature | Film property (film thickness) |
| --- | --- | --- | --- |
| Ex. E-8 | Pb(mohd)$_2$ | 140° C. | lead oxide (60 nm) |

TABLE 9-continued

| | Metal complex compound | Vaporizing temperature | Film property (film thickness) |
|---|---|---|---|
| Ex. E-9 | In(momd)$_3$ | 140° C. | Indium oxide (45 nm) |
| Ex. E-10 | Zr(momd)$_4$ | 120° C. | zirconium oxide (30 nm) |
| Ex. E-11 | Ni(mood)$_2$ | 180° C. | nickel oxide (50 nm) |
| Ex. E-12 | Hf(mopd)$_4$ | 180° C. | hafnium oxide (30 nm) |
| Ex. E-13 | Zr(mopd)$_4$ | 180° C. | zirconium oxide (30 nm) |
| Ex. E-14 | Y(mopd)$_3$ | 180° C. | yttrium oxide (30 nm) |

The results shown in Table 9 indicate that the metal complex compounds of the invention have a good film-forming property.

The invention claimed is:

1. A metal complex compound having a β-diketonato ligand which has an alkoxyalkylmethyl group.

2. The metal complex compound of claim 1, in which the β-diketonato ligand having an alkoxyalkylmethyl group is represented by the formula (1):

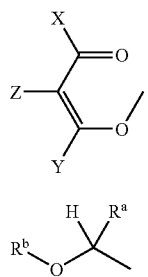

wherein X stands for an alkoxyalkylmethyl having the above-mentioned formula (2) in which each of $R^a$ and $R^b$ independently represents a linear or branched alkyl group having 1 to 5 carbon atoms; Y stands for an alkoxy-alkylmethyl of the above-mentioned formula (2) or a linear or branched alkyl group having 1 to 8 carbon atoms; and Z stands for a hydrogen atom or an alkyl group having 1 to 4 carbon atoms.

3. The metal complex compound of claim 1, which is represented by the formula (3):

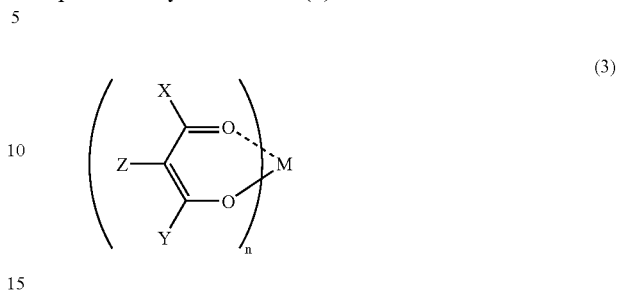

in which M stands for a metal atom; each of X, Y, and Z has the same meaning, and n is an integer of 1 to 4.

4. The metal complex compound of claim 3, in which M is a metal atom described in Periodic Table IIA, IIB, IIIB, IVB or VA.

5. The metal complex compound of claim 3, in which M is an atom of metal selected from the group consisting of magnesium, calcium, strontium, barium, zinc, born, aluminum, gallium, indium, germanium, tin, lead, vanadium, niobium, and tantalum.

6. The metal complex compound of claim 3, in which M is a metal atom described in Periodic Table IVA, VIA, VIIA, or VIII.

7. The metal complex compound of claim 3, in which M is an atom of metal selected from the group consisting of titanium, zirconium, hafnium, chromium, manganese, nickel, cobalt, iron, ruthenium, and iridium.

8. The metal complex compound of claim 3, in which M is a metal atom described in Periodic Table IB, and n is 1 or 2.

9. The metal complex compound of claim 3, in which M is a metal atom selected from the group consisting of a copper atom, a silver atom, and a gold atom.

10. The metal complex compound of claim 3, in which M is a rare earth metal atom, and n is 3 or 4.

11. The metal complex compound of claim 3, in which M is an atom of metal selected from the group consisting of yttrium, lanthanum, cerium, praseodymium, neodymium, samarium, europium, erbium, ytterbium, and lutetium, and n is 3 or 4.

* * * * *

UNITED STATES PATENT AND TRADEMARK OFFICE
CERTIFICATE OF CORRECTION

PATENT NO. : 7,595,414 B2 Page 1 of 1
APPLICATION NO. : 10/592876
DATED : September 29, 2009
INVENTOR(S) : Kadota et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 504 days.

Signed and Sealed this

Twenty-eighth Day of September, 2010

David J. Kappos
*Director of the United States Patent and Trademark Office*